United States Patent [19]
Allen

[11] Patent Number: 5,556,758
[45] Date of Patent: Sep. 17, 1996

[54] HALOPEROXIDASE ACID OPTIMUM CHEMILUMINESCENCE ASSAY SYSTEM

[75] Inventor: Robert C. Allen, Little Rock, Ark.

[73] Assignee: ExOxEmis, Inc., Little Rock, Ark.

[21] Appl. No.: 245,839

[22] Filed: May 19, 1994

Related U.S. Application Data

[63] Continuation of Ser. No. 109,142, Aug. 19, 1993, abandoned, which is a continuation of Ser. No. 830,760, Feb. 3, 1992, abandoned, which is a continuation of Ser. No. 417,276, Oct. 5, 1989, abandoned.

[51] Int. Cl.$^6$ .................................................. G01N 33/535
[52] U.S. Cl. ........................... 435/7.9; 435/7.92; 435/28
[58] Field of Search ........................... 435/7.9, 7.92, 435/7.93, 7.95, 28, 29; 436/518, 800, 805, 808

[56] References Cited

U.S. PATENT DOCUMENTS

| | | | |
|---|---|---|---|
| 3,689,391 | 9/1972 | Ullman | 204/157.91 |
| 3,996,345 | 12/1976 | Ullman et al. | 436/537 |
| 3,998,943 | 12/1976 | Ullman | 436/501 |
| 4,104,029 | 8/1978 | Maier, Jr. | 435/7.4 |
| 4,160,645 | 7/1979 | Ullman | 436/74 |
| 4,161,515 | 7/1979 | Ullman | 436/534 |
| 4,220,450 | 4/1978 | Maggio | 436/537 |
| 4,231,754 | 11/1980 | Vogelhut | 436/172 |
| 4,238,195 | 12/1980 | Boguslaski et al. | 436/534 |
| 4,256,834 | 3/1981 | Zuk et al. | 435/7.72 |
| 4,269,938 | 5/1981 | Frank | 435/7.91 |
| 4,277,437 | 7/1981 | Maggio | 422/61 |
| 4,302,534 | 11/1981 | Halmann et al. | 435/6 |

(List continued on next page.)

FOREIGN PATENT DOCUMENTS

| | | |
|---|---|---|
| 235970 | 9/1987 | European Pat. Off. |
| 0254051 | 1/1988 | European Pat. Off. |

OTHER PUBLICATIONS

Seitz Meth. Enz. vol. LVII pp. 445–463 (1978).
Weeks et al in *Practical Immunoassay* Wilfrid R. Butt Ed, Chapter 5, pp. 103–116, Marcel Decker, Inc. (1984).

(List continued on next page.)

*Primary Examiner*—Margaret Parr
*Assistant Examiner*—Lora M. Green
*Attorney, Agent, or Firm*—Christensen O'Connor Johnson & Kindness PLLC

[57] ABSTRACT

A highly sensitive chemiluminescent indicator system is disclosed for determining the presence or amount of an analyte in a liquid sample. The new acid optimum chemiluminescent indicator system comprises haloperoxidase (halide:hydrogen peroxide oxidoreductase), halide, oxidant and chemiluminigenic substrate. The indicator system acts as a synthesizer of highly reactive singlet molecular oxygen ($^1O_2$), which reacts with the chemiluminigenic substrate to yield an excited state, oxidized reaction product. The excited state reaction product then relaxes to a lower energy (e.g., ground) state with the emission of measurable light in an amount related to the amount of each of the reaction participants present in a reaction solution. Known, non-rate limiting amounts of three of the reaction participants are provided in an assay solution to determine the presence or amount of the fourth participant in a test sample. The fourth participant in the test sample may be the analyte of interest, or may be produced or consumed in the test sample through one or more preliminary reactions involving the ultimate analyte of interest, with the amount of the fourth participant being related to the amount of analyte in the test solution. Accordingly, the indicator system of the invention may be employed for the determination of a wide variety of analytes. The indicator system operates most efficiently over the range from acid to slightly basic pH, e.g., at a pH of about 3 to about 8. Also described is a variety of illustrative assay formats in which the indicator reaction of the invention may be employed, as well as kits for use in carrying out assays utilizing the haloperoxidase/halide/oxidant/substrate indicator system.

40 Claims, 4 Drawing Sheets

U.S. PATENT DOCUMENTS

| | | | |
|---|---|---|---|
| 4,372,745 | 2/1983 | Mandle et al. | 436/537 |
| 4,380,580 | 4/1983 | Boguslaski et al. | 435/5 |
| 4,383,031 | 5/1983 | Boguslaski et al. | 435/7.72 |
| 4,436,715 | 3/1984 | Schaap et al. | 423/579 |
| 4,478,817 | 10/1984 | Campbell et al. | 424/7.1 |
| 4,521,511 | 6/1985 | Stout | 435/28 |
| 4,598,044 | 7/1986 | Kricka et al. | 435/28 |
| 4,647,532 | 2/1987 | Watanabe et al. | 436/172 |
| 4,729,950 | 3/1988 | Kricka et al. | 435/28 |
| 4,849,342 | 7/1989 | Ben-Michael | 435/7.1 |

OTHER PUBLICATIONS

Allen (1) *Biochem. Biophys. Res. Comm.* 63:684–91, 1975.

Allen et al. (2) *Biochem Biophys. Res. Comm.* 69:245–252, 1976.

Weiss et al. *Science* 234:200–202, 1986.

Ford et al., Immunochemistry vol. 15, pp. 237–243 (1978).

Seitz, W. R., "Chemiluminescence Detection of Enzymically Generated Peroxide", *Methods in Enzymology*, LVII, 445–462, 1978.

Klebanoff, "Myeloperoxidase–Halide–Hydrogen Peroxide Antibacterial System," *J. Bacteriol.*, 95, 2131–2138, 1968.

Allen, R. C., Dissertation entitled "Studies on the Generation of Electronic Excitation States in Human Polymorphonuclear Leukocytes and their Participation in Microbicidal Activity", Jul. 1973.

Allen, R. C. et al., "Evidence for the Generation of an Electronic Excitation State(s) in Human Polymorphonuclear Leukocytes and its Participation in Bactericidal Activity", *Biochemical and Biophysical Research Communications*, 47(4), 679–684, 1972.

Allen, R. C., "Halide Dependence of the Myeloperoxidase–mediated Antimicrobial System of the Polymorphonuclear Leukocyte in the Phenomenon of Electronic Excitation", *Biochemical and Biophysical Research Communications*, 63(3), 675–683, 1975.

Allen, R. C., "Evaluation of Serum Opsonic Capacity by Quantitating the Initial Chemiluminescent Response from Phagocytizing Polymorphonuclear Leukocytes", *Infection and Immunity*, 15(3), 828–833, 1977.

Allen, R. C. et al., "Correlation of Metabolic and Chemiluminescent Responses of Granulocytes from Three Female Siblings with Chronic Granulomatous Disease", *Journal of Infectious Diseases*, 136(4), 510–518, 1977.

Allen, R. C., "Reduced, radical, and excited state oxygen in leukocyte microbicidal activity", In J. T. Dingle, P. J. Jacques and I. H. Shaw [eds.]. Lysosomes in Applied Biology and Therapeutics, North–Holland Publishing Company, 1979, pp. 197–233.

Allen, R. C., "Chemiluminescence: An Approach to the Study of the Humoral–phagocyte Axis in Host Defense Against Infection", In Liquid Scintillation Counting, Recent Applications and Development, vol. II. Sample Preparation and Applications, Academic Press, Inc., 1980, pp. 377–393.

Allen, R. C., et al., "Role of Myeloperoxidase and Bacterial Metabolism in Chemiluminescence of Granulocytes from Patients with Chronic Granulomatous Disease", *Journal of Infectious Disease*, 144(4), 344–348, 1981.

Allen, R. C. et al., "Humoral–Phagocyte Axis of Immune Defense in Burn Patients", *Archives of Surgery*, 117, 133–140, 1982.

Allen, R. C., "Direct Quantification of Phagocyte Activity in Whole Blood: A Chemiluminigenic Probe Approach", In E. Kaiser, F. Gabl, M. M. Muller and P. M. Bayer [eds.] Proceedings of XI International Congress of Clinical Chemistry, Vienna, 1981. Walter de Gruyter, Berlin, New York, 1982, pp. 1043–1058.

Allen, R. C., "Biochemiexcitation: Chemiluminescence and the Study of Biological Oxygenation Reactions", In W. Adam and G. Cilento [eds.] Chemical and Biological Generation of Excited States, Academic Press, Inc., New York, 1982, pp. 309–344.

Allen, R. C., "Chemiluminescence and the Study of Phagocyte Redox Metabolism", In F. Rossi and P. Patrisica [eds.] Biochemistry and Function of Phagocytes, Plenum Publishing Corporation, 1982, pp. 411–421.

Allen, R. C. and M. M. Lieberman, "Kinetic Analysis of Microbe Opsonification Based on Stimulated Polymorphonuclear Leukocyte Oxygenation Activity", *Infection and Immunity* 45(2), 475–482, 1984.

Allen, R. C., "Phagocytic Leukocyte Oxygenation Activities and Chemiluminescence: A Kinetic Approach to Analysis", In Marlene A. DeLuca and William D. McElroy [eds.] Methods in Enzymology, vol. 133, Bioluminescence and Chemiluminescence, Academic Press, Inc., 1986, pp. 449–493.

Allen, R. C., "Oxygen–Dependent Microbe Killing by Phagocyte Leukocytes: Spin Conservation and Reaction Rate", In W. Ando and Y. Moro–oka [eds.] The Role of Oxygen in Chemistry and Biochemistry, Proceedings of an International Symposium on Activation of Dioxygen and Homogeneous Catalytic Oxidations, Tsukuba, Japan, 12–16 Jul. 1987, *Studies in Organic Chemistry*, vol. 33, pp. 425–434, 1988 Elsevier Science Publishers B. V., Amsterdam.

Steinbeck, M. J. and J. A. Roth, "Neutrophil Activation by Recombinant Cytokines", *Reviews of Infectious Diseases*, 11(4), 549–568, 1989.

Malech, H. L. and J. I. Gallin, "Medical Intelligence, Neutrophils in Human Diseases", *New England Journal of Medicine*, 317(11), 687–694, 1987.

Olsson, I. and P. Venge, "The Role of the Human Neutrophil in the Inflammatory Reaction", *Allergy*, 35, 1–13, 1980.

Cooper, N. R., "Assays for Complement Activation", In Robert M. Nakamura and David T. Rowlands [eds.] Clinics in Laboratory Medicine, Advances in Immunopathology, vol. 6, No. 1, pp. 139–155, Mar. 1986, W. B. Saunders Co.

Chenoweth, D. E., "Complement Mediators of Inflammation", In Gordon D. Ross [ed.] Immunobiology of the Complement System, An Introduction for Research and Clinical Medicine, pp. 63–86, Academic Press, 1986.

Fearon, D. T. and L. A. Collins, "Increased Expression of C3b Receptors on Polymorphonuclear Leukocytes Induced by Chemotactic Factors and By Purification Procedures", *J. Immunology* 130(1), 370–175, 1983.

Fearon, D. T. and W. W. Wong, "Complement Ligand–Receptor Interactions that Mediate Biological Responses", *Ann. Rev. Immunol.* 1, 243–271, 1983.

Dure, L. S. and J. J. Cormier, "Studies on the Bioluminescence of *Balanoglossus biminiensis* Extracts, III. A Kinetic Comparison", *Journal of Biological Chemistry*, 239(7), 1964.

Kopecky, K. R., "Synthesis of 1,2–Dioxetanes", In Waldemar Adam and Giuseppe Cilento [eds.] Chemical and Biological Generation of Excited States, Academic Press, 1982, pp. 85–114.

Bronstein, I. et al., "1,2–Dioxetanes: Novel Chemiluminescent Enzyme Substrates. Applications to Immunoassays", *Journal of Bioluminescence and Chemiluminescence*, 4, 99–111, 1989.

McCapra, F. et al., "Luminescent Labels for Immunoassay—From Concept to Practice", *Journal of Bioluminescence and Chemiluminescence*, 4, 51–18, 1989.

Kearns, D. R. and A. U. Khan, "Sensitized Photooxygenation Reactions and the Role of Singlet Oxygen", *Photochemistry and Photobiology*, 10, 193–210, 1969.

Kanofsky, J. R., "Singlet Oxygen Production by Lactoperoxidase", *Journal of Biological Chemistry*, 258(10), 5991–5993, 1983.

Piatt, J. et al., "Singlet Oxygen Formation by a Peroxidase, $H_2O_2$ and Halide System," *Eur. J. Biochem.* 93:323–332 (1979).

Renganathan, V., "Haloperoxidase Reactions Catalyzed by Lignin Peroxidase, an Extracellular Enzyme from the Basidiomycete *Phanerochaete chrysosporium*," *Biochemistry* 26:5127–5132, 1987.

5,556,758

HALOPEROXIDASE ACID OPTIMUM CHEMILUMINESCENCE ASSAY SYSTEM

This application is a continuation based on prior application Ser. No. 08/109/142, filed Aug. 19, 1993 abandoned, which is a continuation of application Ser. No. 07/830,760, filed on Feb. 3, 1992, now abandoned, which is a continuation of application Ser. No. 07/417,276, filed on Oct. 5, 1989, now abandoned.

FIELD OF THE INVENTION

The present invention relates to an improved system for the determination of analytes in a test solution by chemiluminescence analysis. More particularly, the present invention relates to an acid pH optimum, halide dependent analyte analysis system utilizing a haloperoxidase (halide: hydrogen peroxide oxidoreductase, EC 1.11.1.n), an oxidant and a luminescent substrate to generate a chemiluminescent signal indicative of the presence or amount of an analyte in a test sample.

BACKGROUND OF THE INVENTION

Assay systems for determining the concentration of one or more analytes in a test sample with a high degree of accuracy are frequently required. These systems find a wide scope of application ranging from the determination of toxic substances in industrial wastes to the determination of potential contaminants in food supplies. The development of assay systems for analytes in biological fluids, such as serum, plasma, urine and the like, has received much attention due to the need of physicians for accurate, up-to-date information concerning the physiological condition of their patients to assist in diagnostic and therapeutic activities. As a result, assay systems capable of determining the concentration of various analytes in biological fluids with a high degree of accuracy have evolved.

One such system is the well-known radioimmunoassay in which a radiolabel conjugated to an analog of the analyte or an antibody is employed. In its classical form, a known amount of a radiolabeled analog of the analyte is allowed to compete with the analyte for a limited quantity of antibody specific for the analyte. In other forms, the radiolabel may be conjugated to an analyte-specific antibody, which forms a "sandwich" with analyte present in the test sample. Without regard to test format, the radiolabel complexed with the analyte or remaining free in solution is measured as an indication relating either directly or indirectly to the amount of analyte in the test sample. Although highly sensitive radiolabel-based assay systems have been developed, the requirement of radioactive materials, specialized handling procedures and specialized equipment, and the production of radioactive wastes present serious drawbacks to widespread, continuing use of radiolabel-based assays.

The requirement for radioactive materials in the assay art has been decreased by the use of enzyme label materials in place of radiolabels. Typical enzyme immunoassays, for example, follow assay protocols very similar to those employed in corresponding radioimmunoassays, with the amount of enzyme activity, determined colormetrically, varying directly or indirectly with the amount of analyte in a test sample. Widespread use of enzyme labelling systems has significantly reduced the amount of radioactive materials which would otherwise have been employed for clinical assay purposes, but has frequently resulted in loss of assay sensitivity, high background levels and equivocal assay results.

More recently, luminescent indicator reactions have been proposed for use in place of radiolabels or enzyme labels in otherwise conventional assay systems. Luminescent reactions, based on the measurement of light emitted by an assay system component, have been investigated for replacement of radioactive and enzyme labels in immunoassay formats and as a replacement for conventional colorimetric or spectrophotometric indicator reactions, such as in assays for substrates of oxidases and hydrolases. The art has generally recognized two types of luminescent indicator reactions useful in assay systems-fluorescent reactions and chemiluminescent reactions. In fluorescent assay systems, a luminescent molecule is promoted to an excited energy state by the transfer of energy from incident radiation produced by a light source to the luminescent molecule. The molecule thereafter relaxes to a lower energy state with the emission of light in a manner and amount dependent on the amount of the luminescent molecule present in the system. In chemiluminescent assay systems, however, no incident radiation is required. Chemiluminescence is broadly defined as the energy product of reacting two or more chemical reactants to obtain an electronically excited, energy-rich reaction product which relaxes to a lower energy state (e.g., ground state) with the emission of light. Methods for the determination of analytes in solution using chemiluminescent techniques are now well established in the art. Examples of patents describing various chemiluminescent assay systems are set forth below.

U.S. Pat. No. 3,689,391 of Ullman discloses the use of chemical or electrochemical reactions to yield molecules in their electronically excited, energy-rich states, and the transfer of energy from those molecules (energy donors) to reactant molecules (energy receptors) that then undergo photochemical transformation yielding emitted light.

U.S. Pat. No. 4,104,029 of Maier, Jr. discloses a procedure for the assay of biochemically active compounds in biological fluids by combining in an aqueous reaction mixture a medium suspected of containing the compound of interest, a chemiluminescent-labelled ligand and a soluble receptor having sites capable of bonding to the ligand and to the chemiluminescent-labelled ligand. The ligand and the chemiluminescent-labelled ligand then compete for bonding interaction with the ligand receptor (antibody). After equilibrium, the receptor (antibody) is isolated from the medium and measured for chemiluminescence, the amount of chemiluminescent-labelled ligand bound to the antibody being related to the amount of unlabelled ligand in the solution being assayed.

U.S. Pat. No. 4,160,645 of Ullman describes a catalyst-mediated competitive protein binding assay which utilizes a chemiluminescent label conjugated to a ligand analog, a first redox reactant which reacts by one-electron transfer, and a second redox reactant which reacts by two-electron transfer, by comparing the rate of reaction between the first and second redox reactants and the chemiluminescent label with the corresponding rate in an assay solution having a known amount of analyte.

U.S. Pat. No. 4,161,516 of Ullman discloses a double receptor fluorescent immunoassay employing a ligand analog conjugated to a fluorescer, an antibody to the ligand and an antibody to the fluorescer, wherein the amount of fluorescer bound to the antifluorescer is related to the amount of ligand present in an unknown sample and the difference in emission spectrum between unbound fluorescer and fluorescer bound to the antibody.

U.S. Pat. Nos. 4,220,450 and 4,277,437 of Maggio disclose a chemiluminescent competitive protein binding assay wherein a chemiluminescent label is conjugated to one member of an immunological pair, a quencher molecule is conjugated to the other member of an immunological pair and the amount of analyte present in an assay medium is determined by observing the light emitted from the medium.

U.S. Pat. No. 4,231,754 of Vogelhut discloses a multilayer chemiluminescent test device including a solid carrier, a first layer having a first reagent system responsive to the presence of an analyte to produce a reaction product, and a second layer having a second reagent system responsive to the presence of the reaction product to produce luminescence. The second reagent system may include a cyclic hydrazide, such as luminol, a ferric ion, hemoglobin, hematin or microperoxidase product catalyst, and a buffer for maintaining the pH of the chemiluminescent reaction medium at from 8.5 to 12.5.

U.S. Pat. No. 4,238,195 of Boguslaski et al. discloses a specific binding assay for determining a ligand, such as an antigen or an antibody, by chemically exciting a fluorescent label and measuring light emitted by the label. The fluorescent label is chemically excited by exposure to a high energy intermediate such as hydrogen peroxide and either oxylochloride, an oxamide or a bis-oxylate ester.

U.S. Pat. No. 4,269,938 of Frank discloses a peroxidase assay conducted by contacting a sample with diacetyl dichlorofluorescin and a source of hydrogen peroxide to form a fluorescent product. When all reactants other than peroxidase are present in excess, the rate of fluorescence increase is related to the amount of peroxidase in the sample assayed.

U.S. Pat. No. 4,302,534 of Halmann et al. discloses a heterogeneous immunoassay in which chemiluminescence is produced by an enzymatic catalyzed redox reaction between hydrogen peroxide and a phenolic compound, such as pyrogallol, resorcinol, phloroglucinol or hydroquinone. In the assay, horseradish peroxidase, lactoperoxidase, turnip peroxidase or potato peroxidase is conjugated to an antibody or antigen, the conjugate is reacted with a sample, excess conjugate is removed, luminescent substrate is added and then light emitted from the system is measured.

U.S. Pat. No. 4,372,745 of Mandell et al. discloses a system for the detection of a biological analyte, including a microencapsulated fluorescer material conjugated to an immunological binding partner specific to the analyte, means for disrupting the capsule and an energy source other than electromagnetic radiation capable of activating a fluorescer.

Chemiluminescent assay systems, particularly those catalyzed by horseradish peroxidase, have been widely reported and are known to have a number of significant advantages over other conventional signal labels commonly used in the art, including relatively high sensitivity, low cost, extended linear range, relatively simple signal measuring equipment and the lack of use of radioactive isotopes, thereby eliminating the need for safety equipment and special handling procedures. Despite these advantages, the use of chemiluminescent assay systems has not been without problems. For example, peroxidase catalyzed oxidations of luminol are highly sensitive to changes in pH. Conventional horseradish peroxidase (HRP) chemiluminescent luminol oxidations are typically conducted at a pH in the range of 8 to 12, with the most efficient chemiluminescence being produced at a pH of about 10.4 to 11.5. The HRP-catalyzed dioxygenation of luminol to produce chemiluminescence is a highly complex process, involving the reaction of HRP with hydrogen peroxide to form a first complex (Complex I), which in turn reacts with luminol to yield a second complex (Complex II) and an oxidized luminol radical. Complex II then reacts with a second luminol molecule to yield a second oxidized luminol radical and HRP in its initial state. In essence, two luminol molecules (2LH$_2$) are dehydrogenated from the hydrazide to yield two luminol radicals (2LH·) according to the reaction:

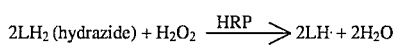

$$2LH_2 \text{ (hydrazide)} + H_2O_2 \xrightarrow{\text{HRP}} 2LH\cdot + 2H_2O$$

The radicals are then believed to react with additional hydrogen peroxide to form aminophthalate with the release of nitrogen and emission of a photon (hv) of light as follows:

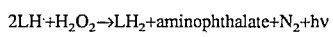

$$2LH\cdot + H_2O_2 \rightarrow LH_2 + \text{aminophthalate} + N_2 + h\nu$$

The luminescence reaction is best achieved when $H_2O_2$ is present in its conjugate base form, $HO_2^-$. However, the relatively high pKa of $H_2O_2$ (11.6; *Lange's Handbook of Chemistry*, 13th Edition, 1985) dictates a relatively high pH for $HO_2^-$ to be present in significant amounts, as follows.

| RATIO OF [HO$_2^-$] TO [H$_2$O$_2$] AT VARIABLE pH | |
|---|---|
| pH | [HO$_2^-$]/[H$_2$O$_2$] |
| 12.65 | 10 |
| 11.65 | 1 |
| 10.65 | $10^{-1}$ |
| 9.65 | $10^{-2}$ |
| 8.65 | $10^{-3}$ |
| 7.65 | $10^{-4}$ |
| 6.65 | $10^{-5}$ |
| 5.65 | $10^{-6}$ |
| 4.65 | $10^{-7}$ |
| 3.65 | $10^{-8}$ |

For example, the effective concentration of $HO_2^-$ in a one millimolar solution of $H_2O_2$ is one nanomolar at pH 5.65. In order to obtain efficient oxidation of luminol, it has therefore been a common practice to conduct HRP-catalyzed oxidation at alkaline pH levels, particularly at a pH of about 7 to 12, and more commonly at a pH of 9 to 11. At high pH levels, however, luminol undergoes base catalyzed oxidation even in the absence of a catalytic enzyme, resulting in peroxide consumption, high background chemiluminescence and frequently in unacceptably low signal-to-noise ratios.

These pH requirements pose serious limitations to the widespread use of peroxidase catalyzed luminol luminescence for clinical and research applications. For example, peroxidase catalysis is most efficient over the pH range of 7 to 9; above a pH of 9, peroxidase exhibits substantially lower activity. However, oxidase enzymatic reactions typically exhibit an optimum pH in the range of about 5 to about 7. When oxidase enzymatic reactions are employed to produce hydrogen peroxide for measurement by a peroxidase catalyzed indicator system, the primary enzymatic processes producing hydrogen peroxide cannot occur simultaneously with the luminescent reaction (where a significantly higher pH is optimum) without severe compromises to luminescent intensity and the rates of the enzyme-catalyzed reactions. In addition to increasing the background chemiluminescence, the relatively high pH levels required for the peroxidase catalyzed luminescent reaction may accelerate the rate of reaction between hydrogen peroxide and reducing components in the biological sample, thereby consuming hydrogen peroxide before it can react with luminol, decreasing the observed luminescence from the system and artificially interfering with accurate measurement of the arialyre of interest. See Seitz, W. R., "Chemiluminescence Detection of Enzymatically Generated Peroxide", *Meth. Enzymol.*, 57: 445–462 (1978).

U.S. Pat. No. 4,598,044 of Kricka et al. discloses an enhanced luminescent reaction between a peroxidase enzyme, an oxidant and a 2,3-dihydro-1,4-phthalazinedione in which the total light emission from the luminescent reaction is stated to be increased (or the signal/noise ratio is enhanced) by adding certain phenolic compounds into the luminescent reaction mixture. The enhanced assay, however, is still preferably conducted at alkaline pH. The use of phenolic compounds to enhance to accelerate the peroxidase catalyzed oxidation of other lumiphores is also disclosed in U.S. Pat. No. 4,521,511. Although the use of enhancers has been shown to improve luminescent determinations, assay sensitivities and poor signal-to-noise ratios continue to prevent the widespread use of these luminescent systems in the clinical environment.

In the "enhanced" luminescent assay using phenolic enhancers to increase light emission, a further problem has been described with the storage stability of reagents used in the assay when the reagents are maintained at the high pH required for conducting the chemiluminescent reaction. To overcome this problem, European Patent Application Publication No. 235,970 describes maintaining the pH of the reagents in the range of about 3 to about 6 prior to use. However, in the assay system disclosed in this European application, an alkaline buffer must be used during the ehemilumineseent reaction to raise the pH of the reaction mixture to a value in the range of 7 to 9 to obtain efficient light emission.

As is apparent from the foregoing, the pH dependency of the light emitting reaction has significantly limited the usefulness of peroxidase catalyzed chemiluminescent techniques as assays in the past. A strong need exists for improved chemiluminescent indicator systems which will overcome problems and limitations associated with prior art ehemilumineseent assays.

In addition to the luminescent assay systems described above, chemical reactions which produce chemiluminescence have been known to occur naturally in various biological systems. For example, myeloperoxidase (MPO) is an oxidoreductase which makes up as much as 5% by weight of mammalian polymorphonuclear (PMN) leukocytes. The detoxification activity of MPO on diphtheria toxin in the presence of hydrogen peroxide was first described by Agner (*Nature*, Vol. 159, p. 271, 1947), as was its dependence on a halide cofactor (Agner, *J. Exp. Med.*, Vol. 92, p. 334, 1950; Agner, *Rec. trav. chim.*, Vol. 74, p. 373, 1955; Agner, *Abstr. Communs*. 4th Congr. Biochem. Vienna, p. 64, 1958). The antibacterial effect of MPO, a halide and an hydrogen peroxide on *Escherichia coli* or *Lactobacillus acidophilus* has been described by Klebanoff in "Myeloperoxidase-Halide-Hydrogen Peroxide Antibacterial System," *J. Baeteciol.*, Vol. 95, pp. 2131–2138 (1968). The antibacterial activity of MPO in the MPO-haldine-hydrogen peroxide system is accompanied by a native (i.e., no chemiluminigenic substrate added) chemiluminescence (Allen,"Studies on the Generation of Electronic Excited States in Human Polymorphonuelear Leukoeytes and Their Participation in Microbiocidal Activity," Dissertation, Tulane University, Jul. 13, 1973), which is pH dependent (Allen, "The Role of pH in the Chemiluminescent Response of the Myeloperoxidase-Halide-HOOH Antimicrobial System," *Biochem. and Biophys. Res. Comm.*, Vol. 63, No. 3, pp. 684–691, 1975) and halide dependent (Allen, "Halide Dependence of the Myeloperoxidase-Mediated Antimicrobial System of the Polymorphonuclear Leukocyte in the Phenomenon of Electronic Excitation," *Biochem. and Biophys. Res. Comm.*, Vol. 63, No. 3, pp. 675–683, 1975).

The oxidoreductase eosinophil peroxidase (EPO) is present in high concentration in eosinophils and has been shown to have an antiparasitic function similar to that of MPO (Caulfield et al., *J. Cell. Biol.*, Vol. 86, pp. 64–76, 1980). EPO catalyzes the oxidation of chloride ion to hypochlorous acid in the presence of hydrogen peroxide at acid pH (Ben et al., "Some Properties of Human Eosinophil Peroxidase, A Comparison With Other Peroxidases," *Biochim. et Biophys. Acta*, Vol. 784, pp. 177–186, 1984). Other chloroperoxidases are known and have been characterized in the literature, such as that isolated from the mold *Caldariomyces fumago* as described by P. D. Shaw and L. P. Hager (*JACS*, Vol. 81, No. 1001, p. 6527, 1959; *JBC*, Vol. 234, p. 2560, 1959, Vol. 234, p. 2565, 1960, and Vol. 236, p. 1626, 1961).

Although the in vivo native MPO/EPO-halide-HOOH antibacterial system (without added chemiluminigenic substrate) has been studied and reported in the literature, the use of a haloperoxidase-halide-oxidant-luminescent substrate indicator system for the determination of the presence or amount of an analyte in a sample has not been reported or suggested in the art.

SUMMARY OF THE INVENTION

It has now been discovered that a highly sensitive chemiluminescent indicator system may be employed to determine the presence or amount of an analyte in a liquid sample, without many of the disadvantages inherent in conventional chemiluminescent indicator systems. The new acid optimum chemiluminescent indicator system comprises haloperoxidase (halide:hydrogen peroxide oxidoreductase), halide, oxidant and chemiluminigenic substrate. The indicator system acts as a synthesizer of highly reactive singlet molecular oxygen ($^1O_2$), which reacts with the chemiluminigenic substrate to yield an excited state, oxidized reaction product. The excited state reaction product then relaxes to a lower energy (e.g., ground) state with the emission of measurable light. Suitable haloperoxidase for use in the indicator system of the invention include myeloperoxidase (MPO), eosinophil peroxidase (EPO), lactoperoxidase (LPO) and chloroperoxidase (CPO). Suitable halides include bromide, chloride or iodide, preferably bromide or chloride when the haloperoxidase is MPO or CPO and bromide when the haloperoxidase is EPO or LPO. The oxidant is preferably a peroxide, most preferably hydrogen peroxide. Useful chemiluminigenic substrates include substrates which are catalytically oxidized (i.e., dioxygenated) by singlet molecular oxygen, by hypohalite, or by hypohalite and peroxide to obtain an excited state oxidized reaction product that relaxes to a lower energy state with the emission of measurable light. Preferred chemiluminigenic substrates include endoperoxide precursors, e.g., cyclic hydrazides, and dioxetane precursors.

The amount of light emitted by the indicator system is related to the amount of each of the reaction participants present in a reaction solution. Thus, known, non-rate limiting amounts of three of the reaction participants are provided in an assay solution to determine the presence or amount of the fourth participant in a test sample. The fourth participant in the test sample may be the analyte of interest, or may be produced or consumed in the test sample through one or more preliminary reactions involving the ultimate analyte of interest, with the amount of the fourth participant being related to the amount of analyte in the test solution. Accordingly, the indicator system of the invention may be employed for the determination of a wide variety of analytes.

In addition to being highly sensitive, the indicator system of the invention operates most efficiently over the range from acid to slightly basic pH, thereby avoiding the problems of prior art basic chemiluminescent reaction conditions heretofore described. Preferably, the indicator reaction of the invention is conducted at a pH of about 3 to about 8, more preferably from a pH of about 4.0 to about 7.0.

Also described is a variety of illustrative assay formats in which the indicator reaction of the invention may be employed, as well as kits for use in carrying out assays utilizing the haloperoxidase/halide/oxidant/substrate indicator system of the invention.

BRIEF DESCRIPTION OF THE DRAWINGS

FIG. 3A indicates that a straight line is not obtained in a standard double reciprocal plot of $v_{CL}$ vs. hydrogen peroxide concentration, as would be expected if the relationship were first order. FIG. 3B indicates that a near straight line relationship is obtained by plotting the reciprocal of the hydrogen peroxide concentration versus the reciprocal of the square root of $v_{CL}$, i.e., that the reaction is second order with respect to hydrogen peroxide concentration. By comparison, FIG. 3C (prior art) shows a first order relationship with respect to hydrogen peroxide concentration in a conventional horseradish peroxidase (HRP) catalyzed system.

DETAILED DESCRIPTION OF THE INVENTION

The present invention is broadly directed to the use of a haloperoxidase dependent indicator system to generate measurable chemiluminescence indicative of the presence or amount of an analyte in a sample. Primary reactants in the indictor system of the invention comprise an oxidant, a halide cofactor and a chemiluminigenic substrate. A haloperoxidase, preferably myeloperoxidase (MPO) or eosinophil peroxidase (EPO), operates to catalyze the production of chemiluminescence in the acid to mildly basic pH range, providing a highly sensitive analyte measurement system with high signal-to-noise ratios.

Haloperoxidase, as used in the practice of the invention, serves as a halide ($X^-$):hydrogen peroxide oxidoreductase. The reaction catalyzed can be considered as two redox half reactions. Halide is oxidized to the corresponding hypohalite ($OX^-$) and 2 reducing equivalents ($H^+ + e^-$):

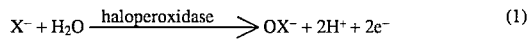

$$X^- + H_2O \xrightarrow{\text{haloperoxidase}} OX^- + 2H^+ + 2e^- \quad (1)$$

An oxidant, such as hydrogen peroxide, is reduced by the two reducing equivalents to yield water:

$$H_2O_2 + 2H^+ + 2e^- \rightarrow 2H_2O \quad (2)$$

The net reaction (i.e., the sum of reactions (1) and (2)) is the haloperoxidase catalyzed production of hypohalite from hydrogen peroxide and halide:

$$H_2O_2 + X^- \xrightarrow{\text{haloperoxidase}} OX^- + H_2O \text{ (Net of 1 and 2)} \quad (3)$$

Figure 1:
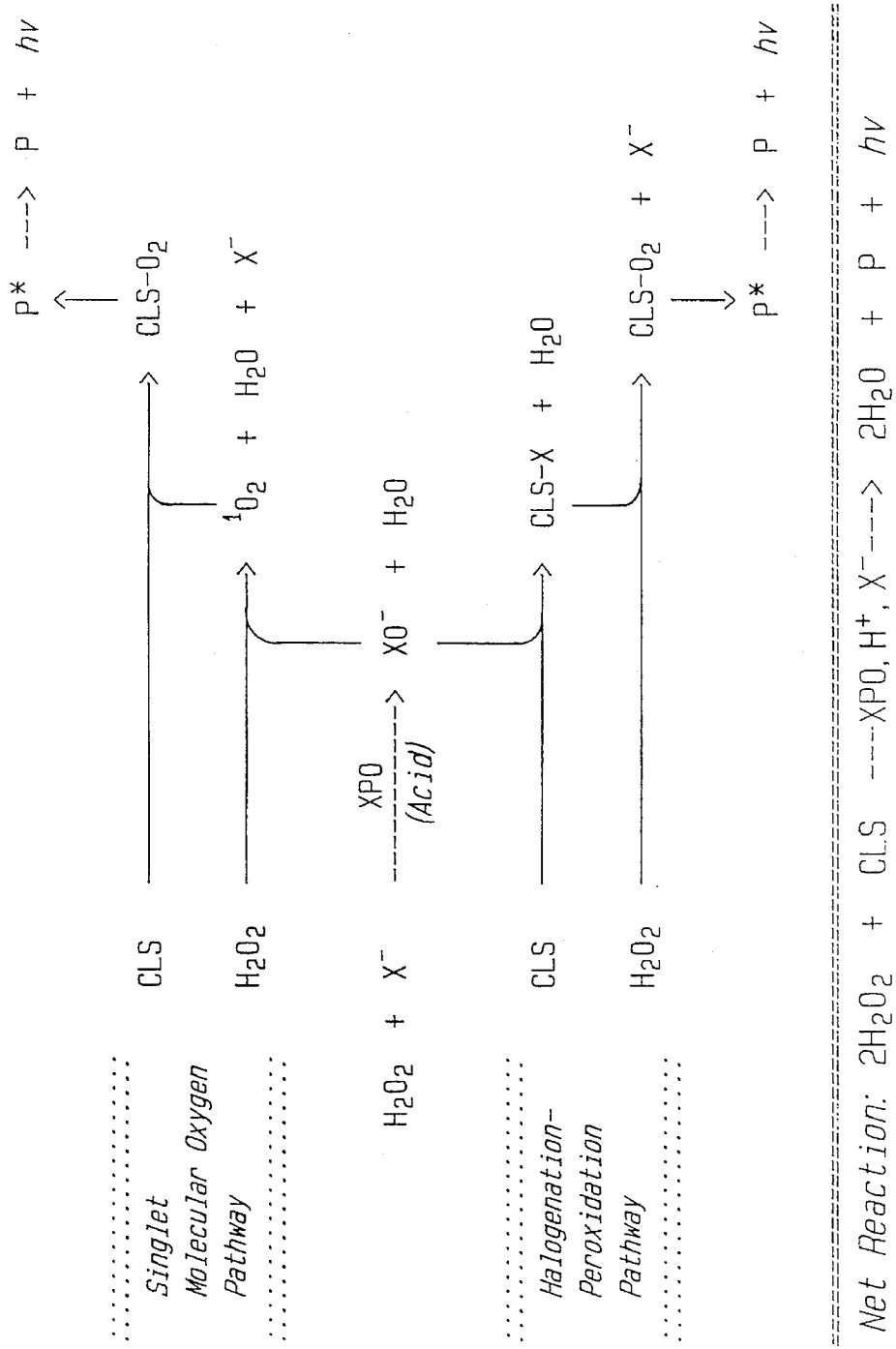
FIG. 1 is a schematic representation of the indicator system of the invention, in which hydrogen peroxide is employed as a representative oxidant.

The hypohalite produced in the indicator system can potentially react following two alternate pathways, as shown in FIG. 1. In the first pathway, identified as the singlet molecular oxygen pathway in FIG. 1, the hypohalite reacts with an additional hydrogen peroxide molecule to yield the halide and singlet multiplicity molecular oxygen ($^1O_2$), a highly reactive molecular species of oxygen that can participate as an electrophil in spin allowed oxygenation reactions, in accordance with the reaction mechanism for production of singlet oxygen disclosed in Kasha et al., "The Physics, Chemistry and Biology of Singlet Molecular Oxygen," *Annals of the New York Academy of Sciences*, Vol. 171, pp 7–23, 1970, the disclosure of which is incorporated herein by reference. The production of singlet molecular oxygen from hypohalite may be represented as follows:

$$H_2O_2 + OX^- \rightarrow X^- + H_2O + {}^1O_2 \quad (4)$$

The net reaction resulting from reactions (3) and (4) is the reaction of two molecules of hydrogen peroxide in the presence of a haloperoxidase and a halide cofactor to yield one molecule of singlet molecular oxygen:

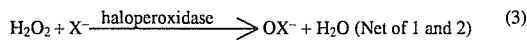

$$2H_2O_2 \xrightarrow{\text{haloperoxidase}/X^-} 2H_2O + {}^1O_2 \text{ (Net of 3 and 4)} \quad (5)$$

Singlet molecular oxygen produced in the system is then reacted with a suitable chemiluminigenic substrate (CLS), such as a cyclic hydrazide to yield an endoperoxide intermediate, or with any of a number of known organic molecular substrates that react with singlet molecular oxygen to yield a dioxetane or a dioxetanone intermediate. These high energy, dioxygenated intermediates undergo cleavage to yield an electronically excited carbonyl moiety that: 1) relaxes to a lower energy state with the emission of light, or 2) transfers its energy to another molecule, which in turn relaxes to a lower energy state with the emission of light.

In the alternative pathway, identified as the halogenation-peroxidation pathway in FIG. 1, the hypohalite produced in reaction (3), above, reacts directly with the chemiluminigenic substrate to yield halogenareal chemiluminigenic substrate (CLS-X), which then reacts with hydrogen peroxide to yield the high energy, dioxygenated intermediate as described above. For either pathway, the oxidation of the substrate and production of light may be represented as:

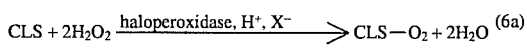

$$CLS + 2H_2O_2 \xrightarrow{\text{haloperoxidase, } H^+, X^-} CLS-O_2 + 2H_2O \quad (6a)$$

$$CLS-O_2 \rightarrow P^* \quad (6b)$$

$$P^* \rightarrow P + h\nu \quad (7)$$

where CLS is the chemiluminigenic substrate, CLS-O$_2$ is the dioxygenated intermediate (e.g., peroxide, endoperoxide, dioxetane or dioxetanone), P* is the high-energy reaction product, P is the lower energy state reaction product and hv is a photon (or emitted light quantum). The overall net reaction of the indicator system of the invention resulting from reactions (5)–(7) may be represented as:

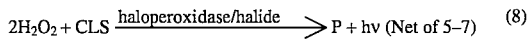
$$2H_2O_2 + CLS \xrightarrow{\text{haloperoxidase/halide}} P + hv \text{ (Net of 5-7)} \quad (8)$$

The amount of light, hv, emitted by the indicator system is related to the amount of each of the primary reaction participants—oxidant, haloperoxidase, halide and chemiluminigenic substrate—present in the reaction mixture. Accordingly, by providing known, non-limiting quantities of any three of the primary participants under suitable reaction conditions, the presence or amount of the fourth primary participant can be readily determined by measuring light emitted (energy product) from the system and comparing the measured response with that from a standard containing known amounts of the limiting reactant. In addition to one of the four primary participants, other analytes may be measured by the indicator system of the invention through one or more preliminary reactions which result in the production or consumption of one of the four primary participants, as is more fully described below. The foregoing reaction mechanism is depicted schematically in FIG. 1, in which hydrogen peroxide is illustrated as a presently preferred oxidant, and X$^-$, OX$^-$, CLS, P* and P have the meanings defined above.

Haloperoxidase useful in the present invention are defined as halide: hydrogen peroxide oxidoreductase (e.g., EC No. 1.11.1.7 and EC No. 1.11.1.10, under the International Union of Biochemistry) for which halide is the electron donor or reductant and peroxide is the electron receiver or oxidant. Any haloperoxidase which catalyzes the halide dependent luminescent reaction of a suitable chemiluminigenic substrate, for example, a 2,3-dihydro-1,4-phthalazinedione such as luminol, may be used in the practice of the present invention. Suitable haloperoxidase, as demonstrated herein, include myeloperoxidase (MPO), eosinophil peroxidase (EPO), lactoperoxidase (LPO) and chloroperoxidase (CPO), with the presently preferred haloperoxidase being myeloperoxidase and eosinophil peroxidase. It has been found that MPO and CPO exhibit similar halide dependent responses, and that EPO and LPO exhibit similar halide dependent responses, as is hereinbelow further described.

The form which the peroxidase enzyme takes in the luminescent reaction of the invention will depend upon the type of assay under consideration. Where the haloperoxidase is used as a label, the peroxidase will be typically coupled to a ligand, such as, for example, a protein, hormone, lectin, hapten, steroid, nucleic acid, metabolite, antigen, antibody, nucleic acid probe, bacteriophage or virus. Generally, the haloperoxidase will be coupled to the ligand through a linking group or bridging arm. Suitable linking groups or bridging arms and coupling procedures will be apparent to those skilled in the art and include those described herein with respect to the coupling of the chemiluminescent substrate to a ligand. In other assay formats, the haloperoxidase enzyme may be free in solution or immobilized on a solid phase or matrix using conventional procedures.

Since the indicator reaction involves the reaction of peroxide and halide to form hypohalite, and the reaction of peroxide and hypohalite to form singlet molecular oxygen ($^1O_2$), as described above, the chemiluminigenic substrate (CLS) used in the practice of the invention may be any substrate which is catalytically oxidized by singlet molecular oxygen ($^1O_2$), by hypohalite or by hypohalite and peroxide, to obtain an excited state oxidized reaction product that relaxes to a lower energy state with the emission of measurable light.

In one presently preferred, illustrative embodiment, the chemiluminigenic substrate may be a cyclic hydrazide that yields peroxide or endoperoxide intermediates under the reaction conditions described herein. Suitable cyclic hydrazides include compounds of the formula:

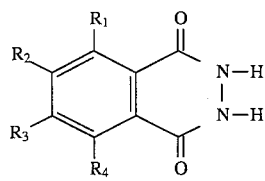

wherein R$_1$ is amino, amido, substituted amino or substituted amido, and R$_2$, R$_3$, R$_4$ are each independently selected from H, optionally substituted C$_1$–C$_6$ alkyl or alkenyl, hydroxyl, C$_1$–C$_6$ alkoxyl, carboxyl, amino, amido, substituted amino or substituted amido, or R$_1$ and R$_2$ taken together are an amino, amido, substituted amino or substituted amido derivative of a benzo group. Presently particularly preferred substrates of this embodiment of the invention are 5-amino-2,3-dihydro-1,4-phthalazinedione (luminol), 6-amino-2,3-dihydro-1,4-phthalazinedione (isoluminol) and 7-dimethylamino-naphthylene-1,2-dicarbonic acid hydrazide.

In general, the cyclic hydrazides undergo electrophilic dioxygenation in the presence of singlet molecular oxygen ($^1O_2$) to produce an unstable peroxide or endoperoxide intermediate, the intermediate rapidly rearranges to the corresponding electronically excited phthalate and the excited-state phthalate relaxes by the emission of light in accordance with the following reaction scheme:

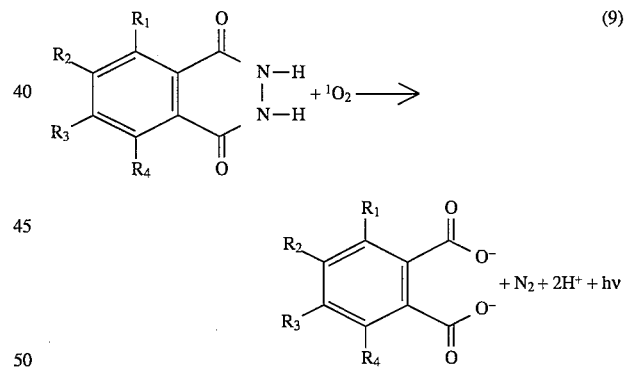

wherein R$_1$–R$_4$ are defined as set forth above.

In another presently preferred, illustrative embodiment of the invention, the chemiluminigenic substrate may be any dioxetane precursor that reacts with singlet molecular oxygen to produce the corresponding unstable or stable 1,2-dioxetane compound. The production of unstable 1,2-dioxetanes is accompanied by rapid dioxetane breakdown yielding electronically excited carbonyl product which relaxes by the emission of light. Stable 1,2-dioxetanes may be generated and stored for later "triggering" of compound degradation and chemiluminescent measurement, as is hereafter further described. Suitable 1,2-dioxetane precursors for use as chemiluminigenic substrates, in the practice of the invention include alkenes lacking reactive allylic hydrogen atoms and enamines, as described in Kopecky, "Synthesis of 1,2-Dioxetanes," *Chemical and Biological Generation of*

*Excited States*, Academic Press, pp. 85–144, 1982, which react with singlet molecular oxygen to produce the corresponding 1,2-dioxetane as follows:

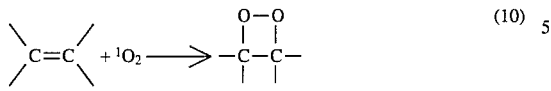
(10)

Representative examples of such dioxetane precursors are known in the art. See, for example, Wieringa et al., *Tetrahedron Lett.*, pp. 169–172, 1972; Bartlett et al., *J. Am. Chem. Soc.*, Vol. 96, pp. 627–629, 1974; Schaap, *Tetrahedron Lett.*, pp. 1757–1760 (1971); Schaap et al., *J. Am. Chem. Soc.*, Vol. 99, pp. 1270 et seq., 1977; Zaklika et al., *J. Am. Chem. Soc.*, Vol. 100, pp. 318–320 and pp. 4916–4918, 1978; and Zaklika et al., *Photochem. Photobiol.*, Vol. 30, pp. 35–44, 1979. The chemiluminigenic substrate may be an alkylene precursor to a stable 1,2-dioxetane compound, such as disclosed in European patent application Publication No. 0254051A2. For example, the chemiluminigenic substrate may be a compound of the formula:

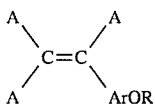

wherein ArOR is an aryl group having an aryl ring substituted with an R-oxy group which forms an unstable oxide intermediate 1,2-dioxetane compound when enzymatically or chemically modified by the removal of the R group. More particularly, the 1,2-dioxetane precursor may be a compound of the formula:

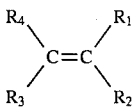

wherein $R_1$ and $R_2$ together and $R_3$ and $R_4$ together can be joined as spirofused alkylene or aryl rings; and $R_1$ is selected from alkyl, alkoxy, aryloxy, dialkyl or aryl amino, trialkyl or aryl silyloxy and aryl groups including spirofused aryl groups with $R_2$; $R_2$ is an aryl group which can include $R_1$ and is substituted with an R-oxy group which forms an unstable oxide intermediate 1,2-dioxetane compound when activated by an activating agent to remove R; $R_3$ and $R_4$ are selected from aryl and alkyl groups which can be joined together as spirofused polycyclic alkyl and polycyclic aryl groups; and the R-oxy group is hydroxy, alkyl or aryl carboxyl ester, inorganic oxy acid salt, alkyl or aryl silyloxy or oxygen pyranosidyl. Specific examples of compounds of this group include (methoxy (2-naphthyl)methylene)adamantane, (6-tert-butyldimethylsilyloxy-2-naphthyl)methoxymethylene)adamantane, [(6-tert-butyldiphenylsilyloxy-2-naphthyl)methorymethylene]adamantane, [(6-acetoxy-2-naphthyl)methoxymethylene]adamantane, [(6-acetoxy-2-naphthyl)methoxymethylene]adamantane, 2-tert-butyl-dimethylsilyloxy-9H-fluoren-9 -ylideneadaman, 3-(tert-butyldimethylsilyloxy)-9H-xanthen-9-ylideneadamantane, 3-hydroxy-9H-xanthen-9-ylideneadamantane, 3-acetoxy-9H-xanthen-9-ylideneadamantane, 3-phosphate-9H-xanthen-9-ylideneadamantane bis(tetraethylammonium) salt, and [(3-tert-butyldimethylsiloxyphenyl)methoxymethylene]adamantane. Alkene dioxetane precursors of this type react with singlet molecular oxygen produced in the practice of the invention to yield stable dioxetanes having relatively long half-lives. Accordingly, by using dioxetane precursors of this type as the chemiluminigenic substrate, the production of a stable dioxetane can be stored over a predetermined time interval, providing a chemical integration of the activity of the indicator system of the invention over the time period. When desired, the chemiluminescent activity of the produced dioxetane may be triggered by the addition of an activating agent, such as an acid, base, salt, enzyme or inorganic or organic catalyst, which labilizes the dioxetane to yield excited carbonyl groups and the associated luminescent activity, as described in European patent application Publication No. 0254051A2. In this manner, assay design for a particular analyte of interest may be optimized by controlling the time interval of dioxetane accumulation and timing of luminescent discharge.

The form which the chemiluminigenic substrate takes in the luminescent reaction of the invention will depend upon the type of assay under consideration. In those assays where the substrate is used as a label, the substrate may be a substituted derivative of the CLS coupled to a ligand such as, for example, a protein, hormone, hapten, steroid, lectin, nucleic acid, metabolite, antigen, antibody, nucleic acid probe, bacteriophage or virus. For example, an amino group of the CLS may be coupled directly to the ligand or may be coupled through a linking group or bridging arm. Suitable linking groups, bridging arms and methods for coupling the substrate to the ligand will be apparent to those skilled in the art and include those groups described in U.S. Pat. Nos. 4,380,580, 4,104,029 and U.K. application Publication No. 2,008,274A. In other types of assays, the substrate may not be coupled to a ligand. In this case, the substrate may be free in solution or immobilized on a solid phase or matrix using conventional procedures.

Presently preferred oxidants for use in the practice of the invention include hydrogen peroxide and alkyl hydroperoxides of the formula:

R—OOH wherein R is hydrogen or a short chain alkyl group having from 1 to 3 carbon atoms. The oxidant activity generally decreases with increasing R chain length, as follows: R=H $>>CH_3>CH_3CH_2>CH_3(CH_2)_2$. The presently particularly preferred oxidant is hydrogen peroxide ($H_2O_2$) due to its highly efficient oxidant activity. In assay formats, such as immunoassays, wherein the chemiluminigenic substrate is conjugated to a ligand for use as a label, a known quantity of the oxidant may be added to the reaction system. In other assay formats, particularly where the reaction system of the invention is coupled to a preliminary reaction system, such as an oxidase catalyzed reaction, which generates the oxidant, particularly hydrogen peroxide, the oxidant may be present in the reaction system as an unknown. In still other assay formats, the oxidant may be coupled to a ligand, or to a solid phase or matrix, using conventional procedures.

The indicator system of the invention is dependent upon the presence of a suitable halide ion. As used herein, the halide may be bromide, chloride or iodide. The selection and amount of halide employed in a particular application will depend upon various factors, such as the haloperoxidase used in the assay system, the pH of the reaction mixture and the magnitude of chemiluminescent response required. It has been found that the more electronegative the halide employed in the system, the greater the concentration of halide required to obtain a given level of chemiluminescent response. See Allen, R. C., "Halide Dependence of the Myeloperoxidase-Mediated Antimicrobial System of the Polymorphonuclear Leukocyte in the Phenomena of Electronic Excitation," *Biochem. and Biophys. Res. Comm.*, Vol. 63, No. 3, pp. 675–683, 1975. The activity of the halides in the indicator system of the invention is generally $Br^->Cl^->I^->>F^-$, with fluoride ion normally producing little or no response. Although the presence of iodide ion may result in the production of measurable luminescence, the known luminescence quenching activity of iodide and its oxidized products limit its desirability for use in some applications, particularly when high levels of sensitivity are required. The choice of halide is further dependent upon the haloperoxidase present in the indicator system. When the haloperoxidase is MPO or CPO, the halide may be bromide, chloride or iodide, preferably bromide or chloride. When the haloperoxidase is EPO or LPO, however, chloride is relatively inefficient as a cofactor, and accordingly, the preferred halide is bromide. When the appropriate haloperoxidase/halide combination is employed and the other members of the indicator system are not rate limiting, the relationship of halide concentration to chemiluminescence is described by the empirical rate equation:

$$velocity_{CL}=I_{max}=K[X^-]^1 \qquad (11)$$

wherein $velocity_{CL}$ is the peak measured velocity of the chemiluminescence response (also described as $I_{max}$, the maximum intensity), k is the proportionality or rate constant and $X^-$ is the halide tested (i.e., $X^-$ is $Cl^-$ or $Br^-$ when the haloperoxidase is MPO or CPO; $X^-$ is $Br^-$ when the haloperoxidase is EPO or LPO). The exponential term "1" indicates that when the other reactants are present in non-rate limiting concentrations, the reaction approximates first order with respect to halide concentration.

In one aspect of the present invention, the presence and amount of MPO and EPO in a test sample can be determined, and MPO and EPO can be distinguished (i.e., differentially quantified), by determining the combined $Br^-$-dependent MPO and EPO luminescence activities of the sample using the indicator system of the present invention. The $Cl_-$-dependent luminescence activity of the sample, which is essentially EPO-independent, is also measured. Under suitable conditions of measurement, the MPO content of the sample is directly proportional to the measured $Br^-$-dependent or $Cl^-$-dependent luminescence, while the EPO content is directly proportional to the $Br_-$-dependent activity minus the $Cl^-$-dependent activity of the sample. Stated differently, the luminescent activity of a test sample under reaction conditions of the invention using $Br^-$ as the sole halide cofactor will quantitatively reflect the activity of both MPO and EPO in the test sample, while the luminescent activity using $Cl^-$ as the cofactor will reflect predominantly the activity of MPO. By forming a ratio of the $Cl^-$-dependent luminescent activity of the sample to the $Br^-$-dependent activity, a quantitative measure is obtained which approaches unity when MPO activity predominates in the test sample and becomes very low when EPO activity predominates. By comparing the measured values with those obtained from standard solutions containing known amounts of MPO and EPO, a highly sensitive method for quantifying the MPO and EPO content of the test sample is obtained.

Since MPO is a major component of polymorphonuclear leukocytes (PMNLs) and blood monocytes and EPO is a major component of eosinophil leukocytes, the capability of halide-dependent differentiation and quantification may be employed to assay for the presence or amount of PMNLs, monocytes and/or eosinophil leukocytes in a biological specimen, such as blood or blood components, tissue biopsy specimens, exudates, as well as secretions and excretions (e.g., urine, sputum and feces) or the like, thereby providing important diagnostic information relating to the nature of the inflammatory process. The amount of neutrophils present in biological fluids is naturally increased by infections, such as osteomyelitis, otitis media, salpingitis, septicemia, gonorrhea, endocarditis, smallpox, ehiekenpox, herpes and Rocky Mountain spotted fever; isehemic necrosis due to myoeardial infarction, burns and carcinoma; metabolic disorders, such as diabetic acidosis, eclampsia, uremia and thyrotoxicosis; stress response due to acute hemorrhage, surgery, excessive exercise, emotional distress, third trimester of pregnancy and childbirth; and inflammatory disease, such as rheumatoid arthritis, acute gout, vasculitis and myositis; and is naturally decreased by bone marrow depression due to radiation or cytotoxie drugs; infections such as typhoid, tularemia, brucellosis, hepatitis, influenza, measles, mumps, rubella, and infectious mononucleosis; hypersplenism from hepatic or storage diseases; collagen vascular disease, such as systemic lupus erythematosis; and deficiencies of folic acid or vitamin $B_{12}$. In contrast, the amount of eosinophils present in biological fluids is naturally increased by allergic disorders, such as asthma, hay fever, food or drug sensitivity, serum sickness and angloneurotic edema; parasitic infestations, such as trichinosis, hookworm, roundworm, and amebiasis; skin diseases, such as eczema, pemphigus, psoriasis, dermatitis and herpes; neoplastic diseases, such as chronic myelocytie leukemia, Hodgkin's disease, metastases and necrosis of solid tumors; and by collagen vascular disease, adrenoeortieal hypofunction, uleerative colitis, polyarteritis nodosa, post-spleneetomy, pernicious anemia, scarlet fever and excessive exercise; and is naturally decreased by stress response due to trauma, shock, burns, surgery and mental distress; and by Cushing's syndrome. Accordingly, the differentiation and quantification of MPO and EPO (and thereby of PMNLs, blood monocytes and eosinophils) using the indicator system of the invention can provide valuable diagnostic information, such as in the diagnosis of bacteria (pyrogenic) infection versus parasitic infestation, and the like.

In a similar manner, CPO and LPO, MPO and LPO, and CPO and EPO can be quantified and differentiated. Thus, assays using two different halide-differentiatable halopecoxidases can be implemented for multiple analyte determinations.

In yet another aspect of the invention, the presence and amount of $Br^-$ and $Cl^-$ in a test sample can be determined, and $Br^-$ and $Cl^-$ can be differentially quantified, by utilizing known amounts of haloperoxidase, determining the combined MPO- (or CPO-) dependent luminescent activity of the sample and determining the EPO- (or LPO-) dependent activity of the sample. Under suitable reaction conditions, the $Br^-$ content of the sample is directly proportional to either the EPO- (or LPO-) dependent activity or the MPO- (or CPO-) dependent activity of the sample, while the $Cl^-$ content of the sample is directly proportional to the MPO- (or CPO-) dependent activity minus the EPO- (or LPO-) dependent activity. In a manner analogous to MPO and EPO differential determinations, a ratio of the EPO- or LPO-dependent activity ($Br^-$-dependent) to the MPO- or CPO-dependent activity ($Cl^-$- and $Br^-$-dependent) may be formed as a useful measure of bromide or chloride in the test sample.

In those applications where the halide is not the analyte, the halide will generally be supplied in non-rate limiting, optimum amounts in the reaction mixture, generally as a salt such as sodium halide, potassium halide, etc. In other applications, the halide may be the analyte, such as in the determination of blood or sweat chloride, or blood bromide in connection with epilepsy therapy.

Analytes to be determined in accordance with the present invention will normally be present in a liquid medium or sample. The sample to be analyzed may be a naturally occurring or artificially formed liquid suspected of containing the analyte. In many cases, the liquid sample will be a biological fluid or a liquid resulting from the treatment or dilution of a biological fluid, such as serum, plasma, urine, feces, and amniotic, cerebral and spinal fluids. Solid materials, such as food, feces or biopsy tissue, and gases may be assayed by the present invention by reducing them to liquid form, such as by dissolution in a liquid, suspension in a liquid or extraction into a liquid. The assays are preferably performed in aqueous solution.

In marked contrast to prior art chemiluminescent indicator systems, particularly those employing peroxidase (e.g., horseradish peroxidase, microperoxidase, etc.) catalyzed luminol oxidation, the indicator system of the invention operates effectively at acid pH. In a preferred embodiment, the indicator system is maintained at a pH in the range of about 3 to about 8, more preferably in the range of about 4 to about 7, during the indicator reactions set forth in reactions (1) to (8), above. By operating at acid pH, a highly sensitive and haloperoxidase-specific indicator reaction is obtained without the base catalyzed background chemiluminescence which has plagued prior art peroxidase chemiluminescent systems. Accordingly, the assay system of the invention may further comprise a suitable buffer solution, for example, a sodium acetate/acetic acid buffer solution, for maintaining an acid pH during the indicator reactions. Any buffers may be employed for this which do not otherwise interfere with the reaction system.

Light or photon emission from the luminescent indicator system of the invention will also be influenced by secondary factors, such as temperature, reagent concentration, mixing speed and method of measurement of emitted light. The precise reaction conditions employed will be generally chosen to optimize overall reaction parameters, including enzyme catalytic activity, reaction kinetics, any apparatus limitations, reaction sensitivity and background noise interference.

The physical characteristics of the light (or photon) emission resulting from the luminescent reaction described herein is primarily dependent upon the nature and properties of the chemiluminigenic substrate, and secondarily on the nature and properties of the haloperoxidase, the oxidant and the halide. When luminol is used as the chemiluminigenic substrate, the maximal spectral emission is in the region of 430–500 nm (blue-green light). The light emission produced in the assay method may be detected by any photosensitive detector having adequate sensitivity in the part of the spectrum in which the luminescent substrate has its maximum spectral emission. Generally, photocells, photodiodes, photoresistors or bialkali photomultiplier tubes having adequate sensitivity over the range of from 350 to 650 nm are suitable for use in the practice of the present invention.

The intensity of light emitted at any particular point in time is proportional to the rate of reaction of the reacting system, and is therefore related to the amount of the unknown in the reaction system. The velocity (dhv/dt) or intensity (I) of the light emitted by the reaction system increases from the base background level when the reaction components and the unknown are mixed, to a maximum value ($I_{max}$) or peak velocity, and thereafter decreases to the base background level as the unknown is consumed. Accordingly, the $I_{max}$ of the system may be used as a relative measure of the presence or amount of the unknown in the reaction mixture. In addition to $I_{max}$, other kinetic expressions of the light emitted by the system may be used to directly or indirectly determine the presence or amount of the unknown in a sample. For example, the total emitted light (i.e., the integral or sum of the number of photons emitted over a predetermined time interval), the peak emitted light intensity, the peak acceleration (i.e., $d^2hv/(dt)^2$ or dv/dt or dI/dt) of light emission or the highest value of velocity or acceleration of luminescence measured within a predetermined time interval can be used as a determinative measure. Accordingly, the apparatus employed for measuring light emitted by the assay system may additionally comprise suitable mechanical or electronic apparatus as may be required for carrying out the measurement, derivatization or integration of the data, data storage and analysis functions, as may be desired.

The haloperoxidase indicator system of the present invention may be employed in a wide variety of assay formats and environments for the determination of the presence or amount of an analyte in a sample, or for the localization of an analyte. For example, the haloperoxidase reaction system may be employed in the determination of the presence or amount of one of the reactants of the assay system, in immunoassays and protein binding assays, in turnover assays, for histological staining, for tracing analytes undergoing redistribution or in other assay formats well known in the art.

Figure 3A:
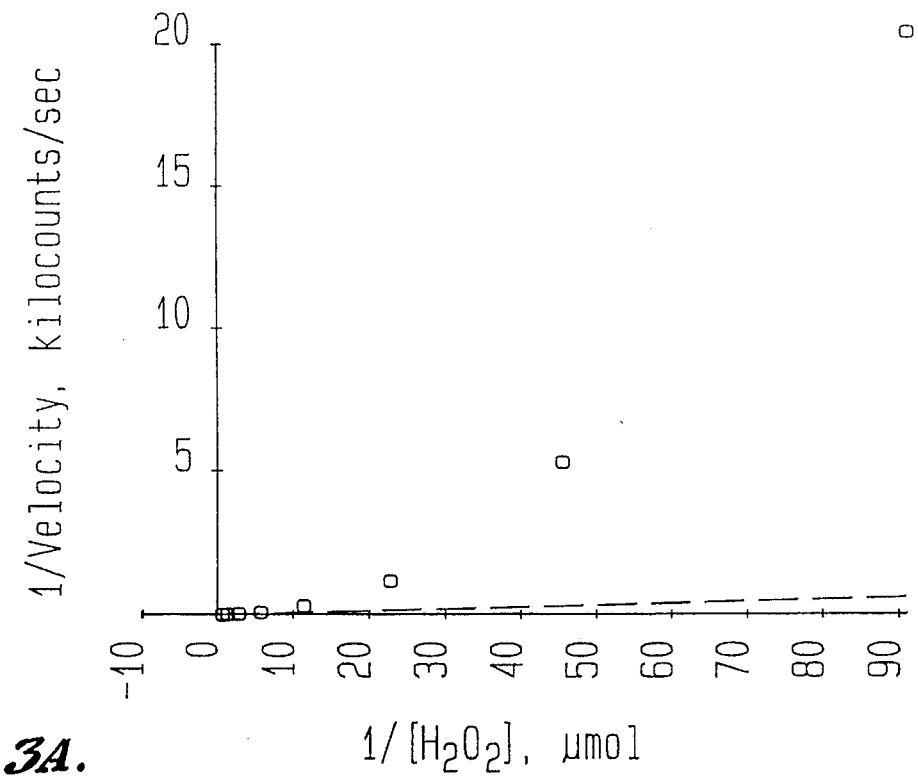
FIGS. 3A and 3B are double reciprocal plots showing the effect of hydrogen peroxide concentration on chemiluminescent velocity ($v_{CL}$, the rate of light emission) in an indicator system of the invention.
Figure 3B:
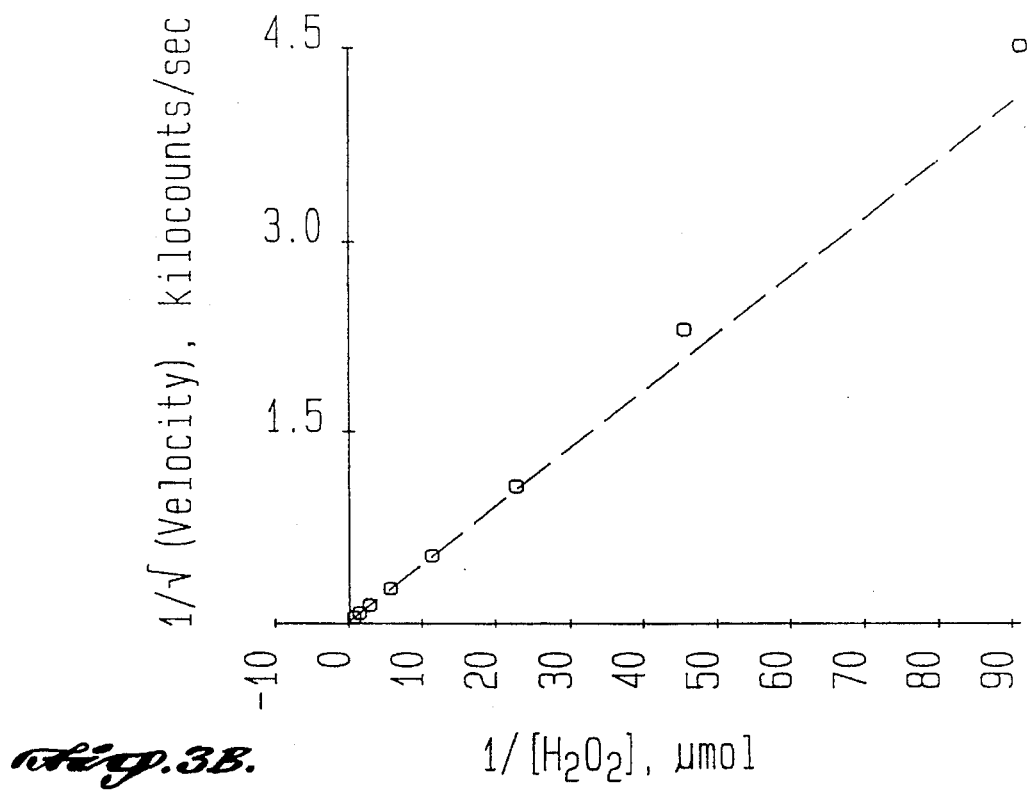
Figure 3C:
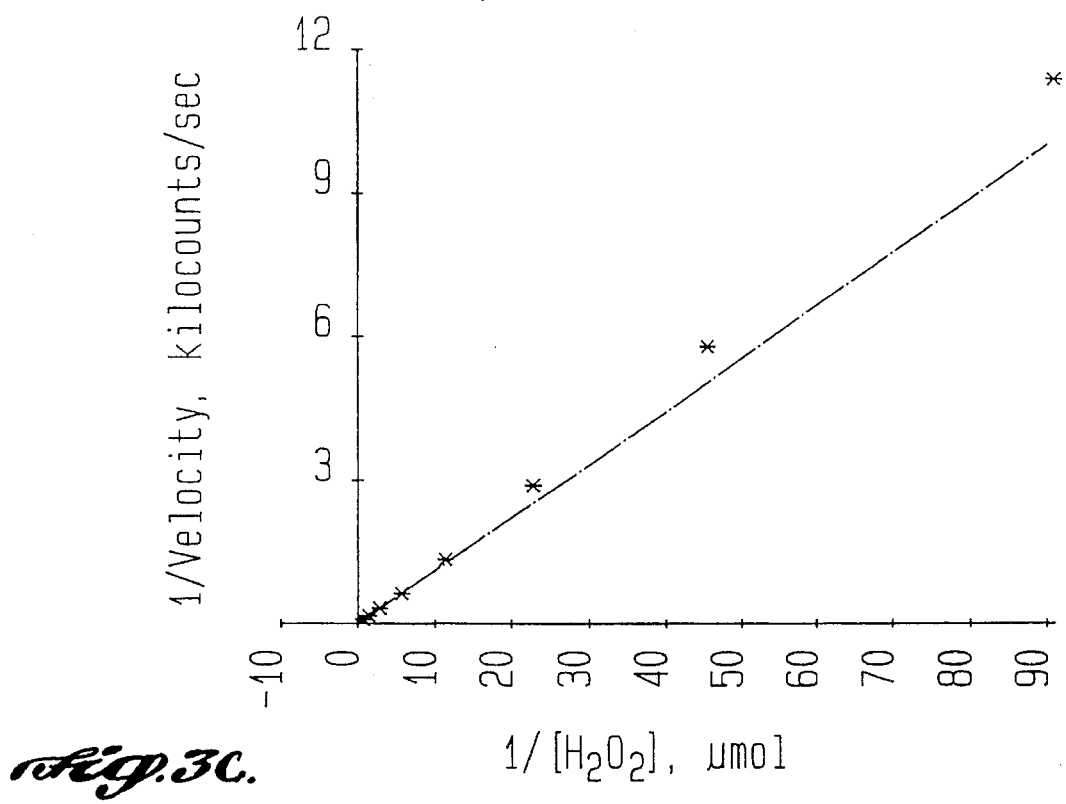

In one embodiment of the invention, the haloperoxidase assay system is employed to determine the presence or unknown amount of oxidant, such as hydrogen peroxide, in a sample. In marked contrast to the non-halide dependent peroxidase catalyzed oxidation of luminol by hydrogen peroxide which is a first order reaction with respect to hydrogen peroxide concentration (see Dure et al., "Studies on the Bioluminescence of *Balanoglossus bimeniensis* Extracts," *J. Biol. Chem.*, Vol. 239, No. 7, pp. 2351–2359, 1964) as shown in FIG. 3C, the haloperoxidase luminescent indicator system of the invention is a second order reaction with respect to hydrogen peroxide concentration, as shown in FIG. 3B. The reaction can be represented by the empirical rate equation:

$$\text{peak velocity}_{CL} = I_{max} = k[H_2O_2]^2 \tag{12}$$

where $I_{max}$ or peak velocity is the peak measured chemiluminescent intensity (velocity) and k is the rate constant or proportionality constant and $[H_2O_2]$ is the hydrogen peroxide concentration. The exponent "2" indicates that, when the other reaction components are not rate limiting, the reaction approximates second order with respect to hydrogen peroxide concentration. Thus, the present reaction system provides a highly sensitive luminescent response proportional to the square of the hydrogen peroxide concentration, as opposed to a directly proportional response obtained in conventional peroxidase catalyzed systems.

In some applications it is desirable to determine the presence or amount of oxidant, such as hydrogen peroxide, naturally present in the sample. Additionally, numerous diagnostic assay systems are known which are based ultimately on the determination of hydrogen peroxide as a measure of activity of hydrogen peroxide generating or consuming enzymes, or of the presence or amount of an analyte substrate for a hydrogen peroxide generating or consuming enzyme. For example, determinations of various analytes such as glucose, galactose, cholesterol, and uric acid are based on the action of specific oxidase enzymes (e.g., glucose oxidase, galactose oxidase, cholesterol oxidase and uricase) to produce hydrogen peroxide, and then the determination of the amount of hydrogen peroxide produced. If the ratio of product peroxide to substrate analyte approximates unity (i.e., when the generation of $H_{22}$ is first order with respect to the substrate analyte), such as, for example, in the case of the glucose/glucose oxidase reaction, and if the primary enzymatic reaction is not limiting, the haloperoxidase indicator system of the invention yields the empirical rate equation:

$$I_{max} = k[\text{analyte substrate}]^2 \qquad (13)$$

where $I_{max}$ and k have the meanings previously described.

Total oxygen as well as $P_{O_2}$ (oxygen partial pressure) can also be measured using this approach. Oxygen is a substrate for oxidases, e.g., glucose oxidases, and as such, the rate of oxygen consumption is quantitatively proportional to the rate of peroxide production. When the other reactants of the system are not rate limiting, oxygen can be quantified as luminescence using the haloperoxide indicator system.

Accordingly, other reaction systems may be coupled with the haloperoxidase indicator system of the invention, such as when an analyte of interest is reacted enzymatically or nonenzymatically to produce a product, which in turn is reacted in one or more additional enzymatic or nonenzymatic steps to ultimately yield or consume hydrogen peroxide or other oxidant, the presence or amount of which is then measured in accordance with the present invention. Thus, in this embodiment, the haloperoxidase indicator system of the invention is broadly applicable to a wide range of analyte determinations in which the analyte is converted in one or more preliminary reactions (or auxiliary reactions) in which hydrogen peroxide (or other oxidant) is produced as a reaction product or is consumed as a reactant, and then the amount of hydrogen peroxide present in the reaction mixture is determined in accordance with the methods disclosed herein as a measure of the presence or amount of the analyte originally present in the sample. Coupled reactions of the invention which produce oxidant may follow the reaction pathway:

$$\text{Analyte} + O_2 \rightarrow OA + H_2O_2 \qquad (14)$$

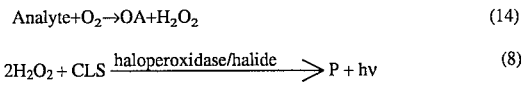

(8)

where OA is the oxidized derivative of the analyte, and CLS and P are as defined above. The analyte may be oxidized directly, such as by the action of an analyte oxidase. Alternatively, the analyte may be subjected to other preliminary reactions forming one or more reaction products which are oxidized in accordance with reaction (14) to form hydrogen peroxide. In still further embodiments, the analyte may be an enzyme, such as an oxidase, whose activity is monitored by the indicator system of the invention. Coupled reactions of the invention which consume oxidant may, for example, follow the reaction pathway:

$$\text{Analyte} + H_2O_2 \rightarrow OA + H_2O \qquad (15)$$

(8)

where OA is the oxidized derivative of the analyte. Again, the analyte may be subjected to other preliminary reactions forming one or more reaction products which are reactive with and consume hydrogen peroxide in accordance with reaction (15). Where the analyte reacts in one or more preliminary reactions to consume hydrogen peroxide, a known amount of hydrogen peroxide will typically be added to the reaction mixture, and the consumption of hydrogen peroxide will be monitored or measured in accordance with the indicator reaction (8).

Representative examples of preliminary oxidant producing reactions coupled with the indicator system of the invention to measure the presence or amount of various analytes are as follows:

Hydrogen Peroxide Producing Preliminary Reactions

Analyte: Glucosce

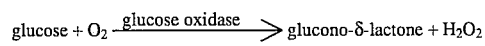

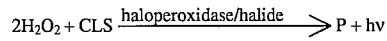

Analyte: Ethanol (and other primary alcohols)

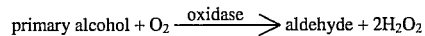

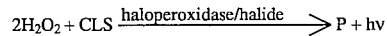

Analyte: Cholesterol

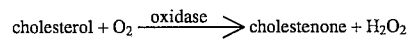

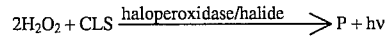

Analyte: Cholinesterase

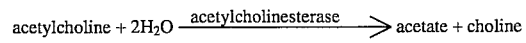

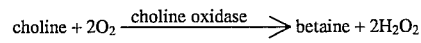

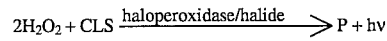

Analyte: Uric Acid

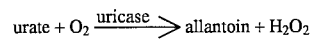

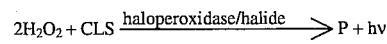

Analyte: Laric Acid (Lactate)

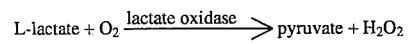

-continued
Hydrogen Peroxide Producing Preliminary Reactions $2H_2O_2 + CLS \xrightarrow{\text{haloperoxidase/halide}} P + h\nu$ Analyte: Pyruvic Acid (Pyruvate)

pyruvate + $PO_4$ + $O_2$ $\xrightarrow{\text{pyruvate oxidase}}$ acetylphosphate + $CO_2$ + $H_2O_2$ $2H_2O_2 + CLS \xrightarrow{\text{haloperoxidase/halide}} P + h\nu$ Analyte: Pyruvic Acid (Alternate Pathway) or NADH pyruvate + $H^+$ + NADH - - - - > L-lactate + $NAD^+$ L-lactate + $O_2$ $\xrightarrow{\text{lactate oxidase}}$ pyruvate + $H_2O_2$ $2H_2O_2 + CLS \xrightarrow{\text{haloperoxidase/halide}} P + h\nu$ Analyte: Lactic Acid or Lactate Dehydrogenase L-lactate + $NAD^+$ $\xrightarrow{\text{lactate dehydrogenase}}$ pyruvate + NADH + $H^+$ pyruvate + $PO_4$ + $O_2$ $\xrightarrow{\text{pyruvate oxidase}}$ acetylphoshaste + $CO_2$ + $H_2O_2$ $2H_2O_2 + CLS \xrightarrow{\text{haloperoxidase/halide}} P + h\nu$ Analyte: Serum Glutamic Pyruvate Transaminase (SGPT) or Alanine Aminotransferase (ALT)

L-alanine + α - ketoglutarate $\xrightarrow{\text{ALT}}$ pyruvate + L-glutamate pyruvate + $PO_4$ + $O_2$ $\xrightarrow{\text{pyruvate oxidase}}$ acetylphosphate + $CO_2$ + $H_2O_2$ $2H_2O_2 + CLS \xrightarrow{\text{haloperoxidase/halide}} P + h\nu$ Analyte: Serum Glutamic Oxalacetic Transaminase (SGOT) or Aspartate Aminotransferase (AST)

L-aspartate + α - ketoglutarate $\xrightarrow{\text{AST}}$ oxaloacetate + L-glutamate oxaloacetate $\xrightarrow{\text{oxaloacetate oxidase}}$ pyruvate + $CO_2$ pyruvate + $PO_4$ + $O_2$ $\xrightarrow{\text{pyruvate oxidase}}$ acetylphosphate + $CO_2$ + $H_2O_2$ $2H_2O_2 + CLS \xrightarrow{\text{haloperoxidase/halide}} P + h\nu$ Analyte: Creatine Kinase (CK)

creatine phosphate + ADP $\xrightarrow{\text{CK}}$ creatin + ATP glycerol + ATP $\xrightarrow{\text{glycerol kinase}}$ glycerol-3-phosphate + ADP glycerol-3-$PO_4$ + $O_2$ $\xrightarrow{\text{glycerol-3-phosphate oxidase}}$ dihydroxy-acetone phosphate + $H_2O_2$ $2H_2O_2 + CLS \xrightarrow{\text{haloperoxidase/halide}} P + h\nu$ -continued
Hydrogen Peroxide Producing Preliminary Reactions Analyte: Creatinine creatinine + $H_2O$ $\xrightarrow{\text{creatininase}}$ creatine creatine + ATP $\xrightarrow{\text{creatine kinase}}$ creatine phosphate + ADP ADP + phosphoenolpyruvate $\xrightarrow{\text{pyruvate kinase}}$ pyruvate + ATP pyruvate + $PO_4$ $O_2$ $\xrightarrow{\text{pyruvate oxidase}}$ acetylphosphate + $CO_2$ + $H_2O_2$ $2H_2O_2 + CLS \xrightarrow{\text{haloperoxidase/halide}} P + h\nu$ Analyte: Creatinine (Alternate Pathway)

creatinine + $H_2O$ $\xrightarrow{\text{creatininase}}$ creatine creatine $\xrightarrow{\text{creatinase}}$ sarcosine + urea sarcosine + $O_2$ $\xrightarrow{\text{sarcosine oxidase}}$ glycine + formaldehyde + $H_2O_2$ $2H_2O_2 + CLS \xrightarrow{\text{haloperoxidase/halide}} P + h\nu$ Analyte: Creatinine (Alternative Pathway)

creatine $\xrightarrow{\text{creatinine iminohydrolase}}$ N-methylhydantoin + $NH_3$ NADH + $NH_4^+$ + 2-oxaglutarate $\xrightarrow{\text{glutamic dehydrogenase}}$ $NAD^+$ + L-glutamate + $H_2O$ $NAD^+$ + L-lactate $\xrightarrow{\text{lactate dehydrogenase}}$ NADH + $H^+$ + pyruvate pyruvate + $PO_4$ + $O_2$ $\xrightarrow{\text{pyruvate oxidase}}$ acetylphosphate + $CO_2$ + $H_2O_2$ $2H_2O_2 + CLS \xrightarrow{\text{haloperoxidase/halide}} P + h\nu$ Analyte: Creatine creatine $\xrightarrow{\text{creatinase}}$ sarcosine + urea sarcosine + $O_2$ $\xrightarrow{\text{sarcosine oxidase}}$ glycine + formaldehyde + $H_2O_2$ $2H_2O_2 + CLS \xrightarrow{\text{haloperoxidase/halide}} P + h\nu$ Analyte: Ammonia $NH_4^+$ + NADH + α-ketoglutarate $\xrightarrow{\text{glutamic dehydrogenase}}$ L-glutamate + $NAD^+$ + $H_2O$ $NAD^+$ L-lactate $\xrightarrow{\text{lactate dehydrogenase}}$ NADH + $H^+$ + pyruvate pyruvate + $PO_4$ + $O_2$ $\xrightarrow{\text{pyruvate oxidase}}$ acetylphosphate + $CO_2$ + $H_2O_2$ -continued
Hydrogen Peroxide Producing Preliminary Reactions $2H_2O_2 + CLS \xrightarrow{\text{haloperoxidase/halide}} P + h\nu$ Analyte: Urea (Blood Urea Nitrogen-BUN)

urea $\xrightarrow{\text{urease}}$ $2NH_4^+ + CO_2$ $NH_4^+ + NADH + \alpha\text{-ketoglutarate} \xrightarrow{\text{glutamic dehydrogenase}}$ L-glutamate + $NAD^+$ + $H_2O$ $NAD^+ + \text{L-lactate} \xrightarrow{\text{lactate dehydrogenase}} NADH + H^+ + \text{pyruvate}$ pyruvate + $PO_4 + O_2 \xrightarrow{\text{pyruvate oxidase}}$ acetylphosphate + $CO_2 + H_2O_2$ $2H_2O_2 + CLS \xrightarrow{\text{haloperoxidase/halide}} P + h\nu$ Generally, the indicator system of the invention may be coupled with any enzymatic reactions producing, in one or more of its reaction steps, an oxidant, such as hydrogen peroxide, operable in the indicator system. Representative examples of such enzymes include, but are not limited to, glycollate oxidase, glucose oxidase, hexose oxidase, cholesterol oxidase, aryl-alcohol oxidase, L-gulonolacetone oxidase, galactose oxidase, pyranose oxidase, L-sorbose oxidase, pyridoxine oxidase, alcohol oxidase, L-2-hydroxyacid oxidase, ecdysome oxidase, choline oxidase, aldehyde oxidase, xanthine oxidase, pyruvate oxidase, oxalate oxidase, glyoxylate oxidase, pyruvate oxidase, D-aspartate oxidase, L-aminoacid oxidase, amine oxidase, pyridoxamine-phosphate oxidase, D-glutamate oxidase, ethanolamine oxidase, tyramine oxidase, putrascine oxidase, sarcosine oxidase, N-methylaminoacid oxidase; N-methyl-lysine oxidase, hydroxylnicotine oxidase, nitroethane oxidase, acetylindoxyl oxidase, urate oxidase, hydroxylamine amine oxidase, and sulphite oxidase.

Representative examples of preliminary oxidant consuming reactions coupled with the indicator system of the invention to measure the presence or amount of various analyte are as follows:

Hydrogen Peroxide Consuming Preliminary Reactions

Analyte: NADH $NADH + H_2O_2 \xrightarrow{\text{NADH peroxidase}} NAD^+ + 2H_2O$ $2H_2O_2 + CLS \xrightarrow{\text{haloperoxidase/halide}} P + h\nu$ Analyte: NADPH $NADPH + H_2O_2 \xrightarrow{\text{NADPH peroxidase}} NADP^+ + 2H_2O$ $2H_2O_2 + CLS \xrightarrow{\text{haloperoxidase/halide}} P + h\nu$ -continued
Hydrogen Peroxide Consuming Preliminary Reactions Analyte: Fatty Acids (e.g., Palmitate)

fatty acid + $2H_2O_2 \xrightarrow{\text{fatty acid peroxidase}}$ fatty aldehyde + $CO_2 + 2H_2O$ $2H_2O_2 + CLS \xrightarrow{\text{haloperoxidase/halide}} P + h\nu$ Analyte: Ferrocytochrome c 2(ferrocytochrome c) + $H_2O_2 \xrightarrow{\text{cytochrome peroxidase}}$ 2(ferrocytochrome c) + $2H_2O$ $2H_2O_2 + CLS \xrightarrow{\text{haloperoxidase/halide}} P + h\nu$ Analyte: Catalase $2H_2O_2 \xrightarrow{\text{catalase}} O_2 + 2H_2O$ $2H_2O_2 + CLS \xrightarrow{\text{haloperoxidase/halide}} P + h\nu$ Analyte: Peroxidase donor + $H_2O_2 \xrightarrow{\text{peroxidase}}$ oxidized donor + $2H_2O$ $2H_2O_2 + CLS \xrightarrow{\text{haloperoxidase/halide}} P + h\nu$ Analyte: Glutathione 2(glutathione) + $H_2O_2 \xrightarrow{\text{glutathionine peroxidase}}$ oxidized glutathionine + $2H_2O$ $2H_2O_2 + CLS \xrightarrow{\text{haloperoxidase/halide}} P + h\nu$ The haloperoxidase indicator system of the invention is also applicable to specific binding assays, such as immunoassays, in which a labelling substance, detectable by the assay system of the invention, is used. Specific binding assays include those systems in which the haloperoxidase is used as a label in homogeneous or heterogeneous assay systems well known in the art, such as those systems described in U.S. Pat. Nos. 3,654,090, 3,817,837, 3,839,153, 3,850,752, 3,879,262, and 4,380,580, or in which the luminescent substrate, oxidant or halide is used as a label in equally well known systems, such as those described in U.S. Pat. Nos. 4,134,792, 4,238,195, 4,238,565, 4,273,866, 4,279,992, 4,372,745, 4,380,580, and 4,383,031.

When used in connection with immunological assays, the analyte to be determined with the indicator system of the invention may be a member of an immunological pair including a ligand and a ligand receptor. By conjugating one component of the indicator system of the invention with a member of the immunological pair, the presence of the analyte in the reaction mixture affects the nature or amount of light produced by the indicator system. The emission of light may then be related, qualitatively or quantitatively, to the presence or amount of the analyte in the sample to be determined. The indicator system of the invention may be employed in any of the direct binding or competitive binding immunological assay techniques known in the art.

In direct binding techniques, a sample suspected of containing the analyte (i.e., the ligand) may be contacted with a conjugate comprising a component of the indicator system and a specific binding partner of the ligand. The activity of the conjugate is then directly related to the extent of binding between the ligand in the sample and the specific binding partner in the conjugate. To obtain quantitative results, the amount of the specific binding partner conjugate is usually provided in excess of that capable of binding with all of the ligand thought to be present in the sample.

In competitive binding techniques, the sample may be contacted with a specific binding partner of the ligand and with a component of the indicator system conjugated to the ligand (or ligand analog). Since any ligand in the sample competes with the ligand (or ligand analog) conjugate for binding sites on the specific binding partner, the chemiluminescent activity of the complexed specific binding partner varies inversely with the extent of binding between ligand in the sample and the specific binding partner. To obtain quantitative results, the amount of specific binding partner employed is typically less than that capable of binding with all of the ligand thought to be present in the sample and all of the ligand (or ligand analog) conjugated to the component of the indicator system.

In either direct or competitive assay formats, the chemiluminescence produced by the indicator system will be indicative of the presence (qualitative) or amount (quantitative) of analyte in the sample. Qualitative determination of the analyte may involve comparing a characteristic of the chemiluminescent reaction with that of a monitoring reaction devoid of the analyte, with any differences being indicative of the presence of analyte in the sample. Quantitative determination of the analyte typically involves comparing a characteristic of the chemiluminescent reaction with that of a monitoring reaction containing known amounts of the analyte. When the assay comprises a separation step, wherein the complex formed between the analyte and its specific binding partner is separated from the reaction mixture, the qualitative or quantitative determination may be made on either the separated or unseparated components of the assay.

By member of an immunological pair is meant that the assay involves two different molecules where one of the molecules has an area on the surface or in a cavity which specifically binds to a particular spatial and/or polar organization of the other molecule. The members of the immunological pair or specific binding partners are commonly referred to in the art as ligand and receptor antiligand). The ligand can be any organic compound for which a receptor naturally exists or can be prepared, typically an antigen or hapten. The receptor (or antiligand) can be any compound or composition capable of recognizing and specifically binding to a discrete portion, e.g., epitope, of the ligand, and may be an antibody, enzyme, Fab fragment, lectin, nucleic acid probe, or the like.

In some embodiments, such as in competitive immunoassays, a ligand analog may be employed which competes with the ligand for binding sites on the receptor. Ligand analogs are typically modified ligands having means to conjugate the analog with another molecule, such as one of the components of the indicator system.

Immunological assays of the invention may also comprise a solid phase for facilitating separation of the analyte from the sample. A suitable solid phase may be any porous or non-porous surface which allows for covalent or noncovalent binding of a member of the immunological pair to its surface. Many suitable solid phase materials are known in the art, such as polymeric materials, such as polystyrene, polyethylene, polypropylene and the like. A wide variety of functional groups may be employed for modifying unreaetive solid phase surfaces for covalent binding of a member of the immunologieal pair, including halides, epoxides, non-oxy-carbonyl moieties, mercaptans, and the like. Binding of the member of the immunological pair may be direct or indirect, for example, through the intermediary of a specific binding pair. The solid phase may be coated or noncoated to aid the binding of the necessary components of the assay to the solid phase, such as with a poly(amino acid), e.g., polylysine, or to inhibit the non-specific binding of sample components to the solid phase. Typical solid phases include container walls, such as the wells of a mierotiter plate, vanes, beads, particles, magnetic beads, magnetic particles, gels, dipsticks, filters, bibulous or non-bibulous matrix materials, and the like. The nature and configuration of the solid phase, including material modifications and configuration, is not critical to the invention as long as the solid phase retains its properties necessary for performance of the assays of the invention.

As will be apparent from the foregoing, the indicator system of the invention is not dependent on any particular assay technique, and is broadly applicable to a wide variety of conventional homogeneous and heterogeneous assay schemes known in the art.

In yet another aspect of the invention, reagents are provided in kit form to facilitate ease of use, reproducibility of results and enhance sensitivity of the assay indicator system. Kits of the invention comprise one or more of the primary indicator system reagents, i.e., haloperoxidase, halide, oxidant and chemiluminescent substrate, in a predetermined form and concentration suitable for dilution or direct use. For use in particular assay systems, such as immunoassays, the kits may further comprise other assay components, including analyte receptors, ligand analogs, solid phase reagents and the like. In addition, kits of the invention may further comprise ancillary materials, such as buffers, diluents, inert proteins, stabilizers and the like, as may be required in the performance of a particular assay.

The foregoing may be better understood in connection with the following representative examples, which are presented for purposes of illustration and not by way of limitation.

EXAMPLES

Stock solutions of assay reagents used in the procedures of the Examples were prepared as follows, unless otherwise noted in the Examples:

An approximate 0.2 mM luminol stock solution was prepared by adding 0.4 ml of 0.5M luminol in dimethylsulfoxide to 1 liter of 50 mM acetate buffer, pH 5.0. The actual final concentration of luminol (i.e., 0.17 mM) was determined by measuring absorbance using an extinction coefficient of 7.6 mM$^{-1}$cm$^{-1}$ at 347 nm (Lee, J. and H. H. Seliger, *Photochem. Photobiol.*, Vol. 15, pp. 227–237, 1972).

Hydrogen peroxide standard concentration solutions were prepared by diluting a 30% $H_2O_2$ stock solution with $H_2O$. The actual final hydrogen peroxide concentration was determined by absorbance using an extinction coefficient of 43.6 M$^{-1}$cm$^{-1}$ at 350 nm (Nobel, R. W. and Q. H. Gibson, *J. Biol. Chem.*, Vol. 245, pp. 2409–2413, 1976).

Myeloperoxidase (MPO) and eosinophil peroxidase (EPO) were prepared from porcine leukocytes. Chloroperoxidase (CPO, E.C. No. 1.11.1.10), lactoperoxidase (LPO) and horseradish peroxidase (HRP) were obtained as a lyophilized powder from Sigma Chemical Co. (St. Louis, Mo., U.S.A.). MPO, EPO, LPO and HRP were reconstituted in 0.15M phosphate buffer solution, pH 7 containing 0.5% Tween 80, dialyzed against the same halide-free phosphate buffer to remove residual halide content, sterile filtered and then stored at 4° C. until use. CPO was reconstituted and handled in a similar manner but without dialysis. Each haloperoxidase (XPO) preparation was determined to be essentially free of contaminating peroxidase or other heme-containing protein. The actual final concentration was determined by dithionite-reduced versus oxidized difference absorbance spectra using absorbance-difference extinction coefficients of 50 mM$^{-1}$cm$^{-1}$ at 473 nm for MPO and 56 mM$^{-1}$cm$^{-1}$ at 450 nm for EPO and LPO (Wever, R. et al., *FEBS Letters*, Vol. 123, pp. 327–331, 1981). HRP was quantified by direct absorbance using an absorbance extinction coefficient of 90 mM$^{-1}$cm$^{-1}$ at 403 nm (Keilin, D. and Hartree, E., *Biochem. J.*, Vol. 49, p 88, 1951).

Unless otherwise specified, all reaction mixtures had a final volume of 1 ml in 50 mM acetate buffer, pH 5, and all measurements were made at ambient temperature, approximately 22° C., using a Berthold CliniLumat LB952 luminometer (Berthold Analytical Instruments, Inc., Nashua, N. H., U.S.A.).

Example 1

Determination of Hydrogen Peroxide

Standard 0.1 ml solutions containing amounts of hydrogen peroxide ranging from 0.011 to 1.407 μmol were prepared by dilution of a $H_2O_2$ stock solution, as described above. To standard hydrogen peroxide solutions in polystyrene test tubes was added 0.5 ml of the stock luminol solution (85 nmol luminol). The luminescent indicator reaction was initiated by adding 0.3 ml of a haloperoxide/halide solution containing MPO (78 pmol) and chloride ion (100 μmol as NaCl) in 50 mM acetate buffer, pH 5, to each test tube and the chemiluminescence velocity (relative counts per second) was measured for the period of from 10 to 60 seconds after addition of the haloperoxidase/halide solution to the hydrogen peroxide/luminol solution. The final reaction volume was 0.9 ml. The peak velocity ($v_{CL}$) is shown in the following Table 1.

TABLE 1

| [$H_2O_2$] (μmol) | $v_{CL}$ (kilocounts/sec.) |
|---|---|
| 1.407 | 431.29 |
| 0.703 | 154.96 |
| 0.352 | 48.56 |
| 0.176 | 13.15 |
| 0.088 | 3.45 |
| 0.044 | 0.87 |
| 0.022 | 0.19 |
| 0.011 | 0.05 |

Figure 2:
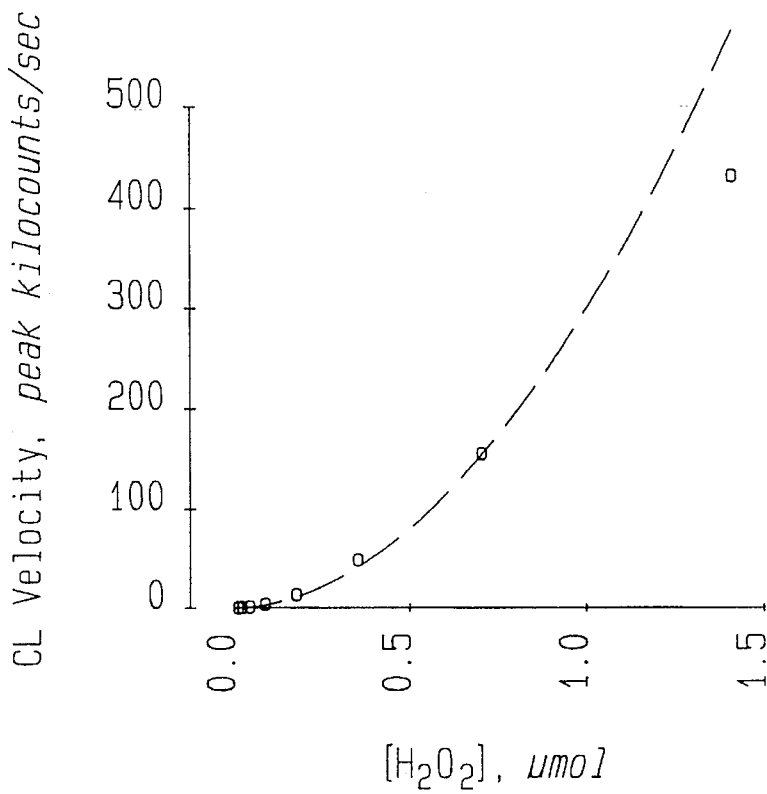
FIG. 2 is a plot showing the effect of hydrogen peroxide concentration on peak chemiluminescent velocity in an indicator system of the invention.

As shown in FIG. 2, a plot of the peak Cl velocity ($v_{CL}$) as a function of hydrogen peroxide concentration for this indicator system results in a hyperbolic curve. A calculation of the rate equation $v_{CL}=k[H_2O_2]^i$ for this indicator system yields a k=300.8 kilocounts/second/μmol hydrogen peroxide and an i=1.90 where i is the order of the reaction with respect to hydrogen peroxide) with a coefficient of determination ($r^2$) of 0.99. The approximate second order nature of this reaction with respect to peroxide concentration is also indicated by the double reciprocal plot of these data. Note that Michaelis-Menten kinetics are not obeyed in the standard plot presented in FIG. 3A. However, for a second order reaction, the square root of $v=c[H_2O_2]^1$ (where c is a proportionality constant relating peroxide concentration to the square root of the velocity)is the equivalent of the equation $v=k[H_2O_2]^2$, and as shown in FIG. 3B, a near straight line relationship is obtained by plotting the reciprocal of the square root of $v_{CL}$ as a function of the reciprocal of the hydrogen peroxide concentration; i.e., the chemiluminescent response approximates second order with respect to hydrogen peroxide concentration when the other components of the indicator system are not rate limiting. The values for the reciprocal of the square root of $v_{CL}$ and the reciprocal of hydrogen peroxide concentration were used to calculate the Km, and the estimated maximum velocity, $V_{max}$, using the method of G. N. Wilkensen, *Biochem. J.*, Vol. 80, pp. 324 et seq., 1961, yielding a Km of 2.82±0.05 (SE) and a $V_{max}$ of 3900±1 (SE) kilocounts/second, wherein SE is the standard error.

The foregoing procedure was repeated substituting bromide ion (5 μmol as NaBr) for the chloride ion in the haloperoxidase/halide solution described above, and substituting EPO (39 pmol), for the MPO in the haloperoxidase/halide solution using either chloride or bromide as the halide. For purposes of comparison, horseradish peroxidase (HRP, 10 pmol) a non-haloperoxidase, was additionally substituted for haloperoxidase in the reaction system. The results are shown in the following Table 2.

TABLE 2

| Reaction Conditions: | | | Rate Equation: | | | Michaelis-Menten | |
|---|---|---|---|---|---|---|---|
| | | | $v = k[H_2O_2]^i$ | | | Kinetic Data: | |
| Enzyme, pmol | $[X^-]$, μmol | [range] $[H_2O_2]$, μmol | (k) | (i) | $(r^2)$ | $K_m \pm SE$ | $V_{max} \pm SE$ |
| MPO, 78 | $Cl^-$, 100 | 0.011–1.4 | 300.8 | 1.90 | 0.99 | * 2.82 ± 0.05 | 3900 ± 1 |
| MPO, 78 | $Br^-$, 5 | 0.011–1.4 | 1616.5 | 1.61 | 0.98 | * 0.58 ± 0.03 | 2932 ± 2 |
| EPO, 39 | $Cl^-$, 100 | 0.011–1.4 | 39.2 | 1.06 | 0.90 | * 0.12 ± 0.01 | 31 ± 0 |
| EPO, 39 | $Br^-$, 5 | 0.011–1.4 | 1073.4 | 1.86 | 0.99 | * 1.45 ± 0.10 | 5310 ± 10 |
| HRP, 10 | $Cl^-$, 100 | 0.011–1.4 | 8.9 | 1.03 | 0.99 | 31.02 ± 6.14 | 280 ± 55 |
| HRP, 10 | $Br^-$, 5 | 0.011–1.4 | 8.6 | 1.03 | 0.99 | 17.49 ± 3.84 | 156 ± 34 |

Reaction was in 50 mM acetate buffer, pH 5.0, containing 85 nmol Luminol, 0.9 ml final volume. The temperature was 22° C.
$V_{max}$ and velocity (v) are expressed in kilocounts/sec.
The * indicates that kinetic calculations are based on the square root of the velocity, $\sqrt{v}$.

As indicated in Table 2, peak CL velocity (v) is quantitatively proportional to the square of the hydrogen peroxide concentration (i) for the MPO and EPO indicator reaction systems; i.e., the chemiluminescence response approximates second order with respect to hydrogen peroxide concentration when the other components of the system are not rate limiting, indicated by the asterisk (*) in Table 2. It is also apparent from Table 2 that chloride ion is substantially less effective as a halide co-factor in the EPO indicator reaction system. As further shown in Table 2, the chemiluminescent response is not second order with respect to hydrogen peroxide concentration for the horseradish peroxidase (HRP) system, and, as such, the calculations were based on standard Michaelis-Menten kinetics. This result is further shown in FIG. 3C, wherein a conventional double reciprocal plot approximates a straight line indicating that the relationship is first order (confirming Dure et al., *J. Biol. Chem.*, Vol. 239, No. 7, pp. 2351 et seq., 1964), and distinct from the haloperoxidase indicator system of the invention.

chloride quantification was determined by following the basic procedure of Example 1 using 0.3 ml of luminol solution (50 nmol luminol), 0.3 ml of halide solution containing from 0.2 to 7.7 μmol of chloride ion (as NaCl) for MPO or from 0.2 to 1000 μmole of chloride ion (as NaCl) for EPO and HRP, 0.1 ml of MPO, EPO or HRP in acetate buffer, pH 5.0, and adding standard 0.3 ml solutions containing amounts of hydrogen peroxide ranging from 0.16 to 6.30 μmol, to trigger the indicator reaction. The final concentration of acetate buffer in the reaction mixture was 50 mM, pH 5.0. The results are shown in the following Table 3.

Example 2

Determination of Chloride

The dependence of the indicator system upon chloride concentration and the potential use of this dependence for

TABLE 3

| Chloride as Primary Variable: Peroxide as Secondary Variable | | | | | | | |
|---|---|---|---|---|---|---|---|
| Reaction Conditions: | | | Rate Equation: | | | Michaelis-Menten | |
| | $[H_2O_2]$ | [range] | $v = k[Cl^-]^i$ | | | Kinetic Data: | |
| Enzyme, pmol: | μmol: | $[Cl^-]$, μmol | (k) | (i) | $(r^2)$ | $K_m \pm SE$ | $V_{max} \pm SE$ |
| MPO, 78 | 6.30 | 0.2–7.7 | 169.2 | 0.74 | 0.99 | 13.5 ± 4.6 | 2173 ± 570 |
| MPO, 78 | 2.52 | 0.2–7.7 | 147.2 | 0.66 | 0.99 | 7.6 ± 2.6 | 1105 ± 253 |
| MPO, 78 | 1.01 | 0.2–7.7 | 95.0 | 0.62 | 0.99 | 5.8 ± 1.7 | 590 ± 103 |
| MPO, 78 | 0.40 | 0.2–7.7 | 42.0 | 0.58 | 0.99 | 3.9 ± 0.8 | 198 ± 20 |
| MPO, 78 | 0.16 | 0.2–7.7 | 18.6 | 0.52 | 0.85 | 0.3 ± 0.1 | 41 ± 5 |
| EPO, 39 | 6.30 | 0.2–1000 | 5.8 | 0.21 | 0.80 | 0.6 ± 0.5 | 17 ± 2 |
| EPO, 39 | 2.52 | 0.2–1000 | 7.8 | 0.20 | 0.89 | 2.5 ± 1.0 | 22 ± 2 |
| EPO, 39 | 1.01 | 0.2–1000 | 8.4 | 0.16 | 0.92 | 1.1 ± 0.4 | 19 ± 1 |
| EPO, 39 | 0.40 | 0.2–1000 | 6.2 | 0.13 | 0.94 | 0.8 ± 0.3 | 12 ± 1 |
| EPO, 39 | 0.16 | 0.2–1000 | 4.7 | 0.09 | 0.75 | 0.2 ± 0.1 | 6 ± 0 |
| HRP, 10 | 2.52 | 0.2–1000 | 0.1 | −0.18 | 0.08 | −0.5 ± 0.7 | 0 ± 0 |
| HRP, 10 | 1.01 | 0.2–1000 | 0.9 | −0.44 | 0.37 | −2.5 ± 14 | 1 ± 1 |
| HRP, 10 | 0.40 | 0.2–1000 | 0.6 | −0.55 | 0.87 | −0.3 ± 0.1 | 0 ± 0 |

Reaction was in 1 ml of 50 mM acetate buffer, pH 5.0, containing 50 nanomoles Luminol.
$V_{max}$ and velocity (v) are expressed in kilocounts/sec.

Figure 4:
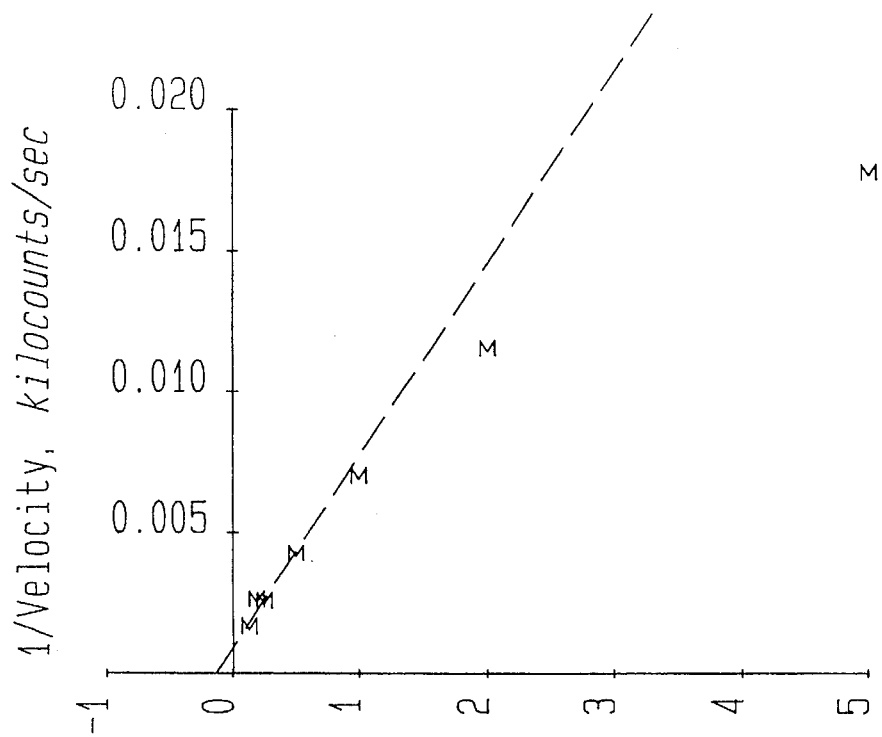
FIG. 4 is a double reciprocal plot showing the effect of chloride concentration on the rate of myeloperoxidase catalyzed light emission in the indicator system of the invention.

From the results shown in Table 3, it is readily apparent that presence of chloride in the reaction mixture can be identified and the quantity of chloride can be readily determined with the indicator system of the invention using MPO as the haloperoxidase. When chloride is used as the halide cofactor, the indicator system using MPO is magnitudinally more efficient than the indicator system using EPO. The reaction using MPO approximates first order with respect to chloride concentration, and as shown in FIG. 4, obeys standard Michaelis-Menten kinetics. Although EPO and HRP data were also considered in FIG. 3, these data did not fall within the plot range. As further shown in Table 3, both MPO and EPO are magnitudinally more efficient under these reaction conditions than HRP, which appears to actually be inhibited by the presence of chloride as indicated by the negative sign of the reaction order, −i.

Example 3

Determination of Bromide

Figure 5:
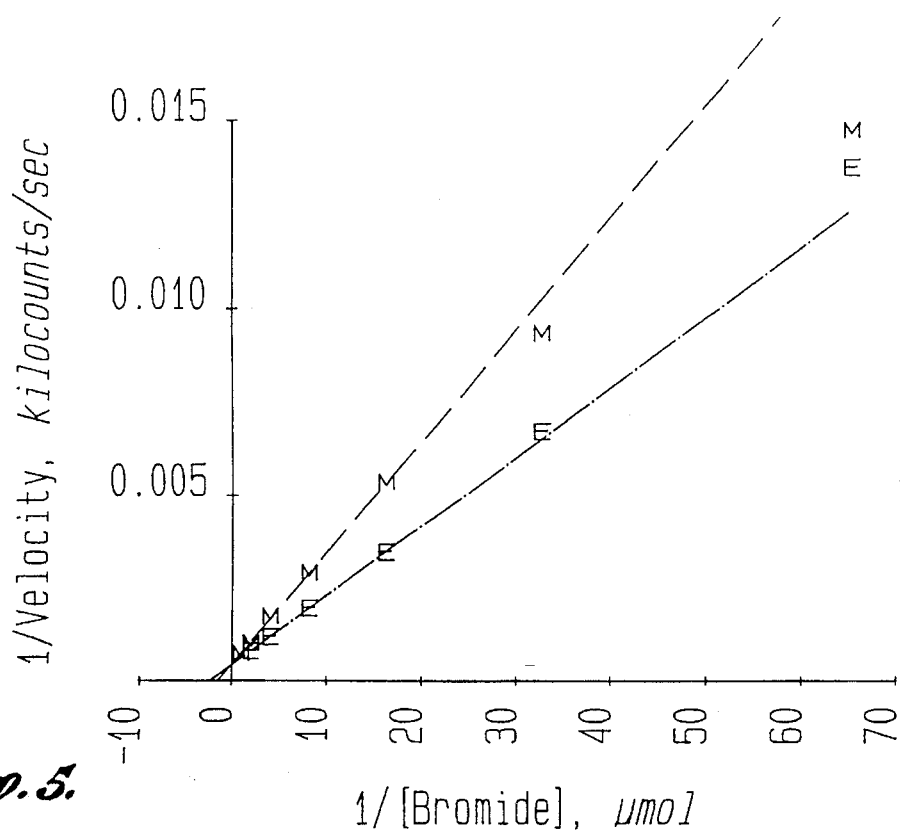
FIG. 5 is a double reciprocal plot showing the effect of bromide concentration on the rate of light emission catalyzed by myeloperoxidase ("M") or eosinophil peroxidase ("E") in the indicator system of the invention.

The dependence of the indicator system upon bromide concentration and the potential use of this dependence for bromide quantification was determined by following the procedure of Example 2 using enzyme/halide solutions containing from 0.015 to 0.98 μmol of bromide ion (as NaBr) for MPO, from 0.015 to 0.49 μmol of bromide ion for EPO and from 0.015 to 1000 μmole of bromide ion for HRP, in place of the chloride ion of Example 2. The results are shown in the following Table 4.

chloride dependence in the MPO system, the reaction approximates first order with respect to bromide concentration for the MPO system and also for the EPO system. FIG. 5 shows standard Michaelis-Menten kinetic characteristics for bromide with either MPO (indicated by capital "M"s in FIG. 5) or EPO (indicated by "E"s in FIG. 5), but not for HRP (none of the data for HRP fall within the plot range of FIG. 4). Under the reaction conditions employed, both MPO and EPO exhibit chemiluminescent activity on the order of four magnitudes greater than the nonhaloperoxidase HRP.

Example 4

Determination of Haloperoxidase

The dependence of the indicator system upon haloperoxidase concentration and the potential use of this dependence for haloperoxidase quantification was determined for the haloperoxidase MPO and CPO, capable of efficiently utilizing both bromide and chloride as halide co-factors, by following the procedure of Example 2 using a standard hydrogen peroxide solution containing 2.5 μmol of hydro-

TABLE 4

| Bromide as Primary Variable: Peroxide as Secondary Variable | | | | | | | |
|---|---|---|---|---|---|---|---|
| Reaction Conditions: | | | Rate Equation: | | | Michaelis-Menten | |
| | $[H_2O_2]$ | [range] | $v = k[Br^-]^i$ | | | Kinetic Data: | |
| Enzyme, pmol: | μmol: | $[Br^-]$, μmol | (k) | (i) | ($r^2$) | $K_m \pm SE$ | $V_{max} \pm SE$ |
| MPO, 78 | 6.30 | 0.015–0.98 | 2113.0 | 0.73 | 0.99 | 0.59 ± 0.03 | 2911 ± 70 |
| MPO, 78 | 2.52 | 0.015–0.98 | 1540.0 | 0.75 | 0.99 | 0.68 ± 0.05 | 2280 ± 96 |
| MPO, 78 | 1.01 | 0.015–0.98 | 916.9 | 0.73 | 0.99 | 0.73 ± 0.05 | 1444 ± 56 |
| MPO, 78 | 0.40 | 0.015–0.98 | 407.4 | 0.70 | 0.99 | 0.61 ± 0.05 | 583 ± 24 |
| MPO, 78 | 0.16 | 0.015–0.98 | 134.4 | 0.60 | 0.85 | 0.37 ± 0.04 | 163 ± 8 |
| EPO, 39 | 6.30 | 0.015–0.49 | 3131.4 | 0.89 | 0.99 | 0.51 ± 0.03 | 2846 ± 116 |
| EPO, 39 | 2.52 | 0.015–0.49 | 2584.9 | 0.82 | 0.99 | 0.44 ± 0.01 | 2351 ± 31 |
| EPO, 39 | 1.01 | 0.015–0.49 | 2058.1 | 0.79 | 0.99 | 0.44 ± 0.02 | 1969 ± 41 |
| EPO, 39 | 0.40 | 0.015–0.49 | 976.5 | 0.70 | 0.99 | 0.29 ± 0.01 | 836 ± 22 |
| EPO, 39 | 0.16 | 0.015–0.49 | 310.5 | 0.56 | 0.98 | 0.13 ± 0.01 | 226 ± 4 |
| HRP, 10 | 2.52 | 0.015–1000 | 1.2 | 0.17 | 0.49 | 6.23 ± 2.68 | 3 ± 0 |
| HRP, 10 | 1.01 | 0.015–1000 | 0.7 | 0.17 | 0.54 | 0.53 ± 0.23 | 2 ± 0 |
| HRP, 10 | 0.40 | 0.015–1000 | 0.5 | 0.10 | 0.53 | 0.08 ± 0.02 | 1 ± 0 |

Reaction was in 1 ml of 50 mM acetate buffer, pH 5.0, containing 50 nanomoles Luminol.
$V_{max}$ and velocity (v) are expressed as peak kilocounts/sec.

As shown in Table 4, the presence of bromide in the reaction mixture can be identified and the quantity of bromide can be readily determined using either MPO or EPO as the haloperoxidase component of the indicator reaction. In marked contrast to the results of Example 2, however, both MPO and EPO are highly efficient when using bromide as the halide cofactor. The ability of MPO to effectively utilize either chloride or bromide as the halide cofactor, while BPO operates most efficiently only in the presence of bromide, can be used for the differential analysis of these halides in a test sample, as well as the differential quantification of MPO and EPO or their origin cells (e.g., neutrophil granulocytes and blood monocytes for MPO, and eosinophil granulocytes for EPO). In a manner similar to gen peroxide to trigger the indicator reaction, and using 0.3 ml of luminol solution containing 125 μmol of luminol, and haloperoxidase solutions (0.1 ml) and halide solutions (0.3 ml, in 150 mM acetate buffer, pH 5.0) containing amounts of MPO ranging from 0.86 to 220 pmol and 6.3, 25 or 100 μmol of chloride; amounts of MPO ranging from 0.024 to 220 pmol and 0.63, 2.5 or 10 μmol of bromide; amounts of MPO ranging from 13.8 to 220 pmol and no halide (as control); and amounts of CPO ranging from 2.7 to 344 pmol and either 0, 6.3, 25 or 100 μmol of chloride or 0.63, 2.5 or 10.0 μmol of bromide. The results are shown in the following Table 5, where $V_{max}$ is expressed in kilocounts/10 seconds.

TABLE 5

| | | Haloperoxidase as Primary Variable: Halide as Secondary Variable | | | | | |
|---|---|---|---|---|---|---|---|
| Reaction Conditions: | | | Rate Equation: | | | Michaelis-Menten | |
| | Halide, | [range] | $v = k[Enzyme]^i$ | | | Kinetic Data: | |
| Enzyme, | μmol | [Enzyme], pmol | (k) | (i) | ($r^2$) | $K_m \pm SE$ | $V_{max} \pm SE$ |
| MPO | Cl⁻, 100 | 0.86–220 | 1.85 | 1.99 | 0.93 | 84 ± 10 | 46846 ± 136 |
| MPO | Cl⁻, 25 | 0.86–220 | 0.94 | 2.11 | 0.96 | 104 ± 11 | 50624 ± 142 |
| MPO | Cl⁻, 6.3 | 0.86–220 | 0.26 | 2.24 | 0.98 | 241 ± 26 | 86068 ± 389 |
| MPO | Br⁻, 10 | 0.024–220 | 14.59 | 1.66 | 0.94 | 31 ± 4 | 31357 ± 49 |
| MPO | Br⁻, 2.5 | 0.024–220 | 10.71 | 1.67 | 0.96 | 47 ± 5 | 35067 ± 55 |
| MPO | Br⁻, 0.63 | 0.024–220 | 2.92 | 1.83 | 0.98 | 109 ± 9 | 50306 ± 82 |
| MPO | none | 13.8–220 | 0.00 | 2.34 | 0.95 | negative | negative |
| CPO | Cl⁻, 100 | 2.7–344 | 1.63 | 1.70 | 0.94 | 128 ± 6 | 26628 ± 12 |
| CPO | Cl⁻, 25 | 2.7–344 | 0.04 | 2.18 | 0.96 | 261 ± 23 | 15633 ± 39 |
| CPO | Cl⁻, 6.3 | 2.7–344 | 0.01 | 2.04 | 0.97 | 849 ± 154 | 12301 ± 281 |
| CPO | Br⁻, 10 | 2.7–344 | 11.94 | 1.37 | 0.97 | 98 ± 7 | 32277 ± 31 |
| CPO | Br⁻, 2.5 | 2.7–344 | 1.28 | 1.62 | 0.98 | 211 ± 17 | 25518 ± 43 |
| CPO | Br⁻, 0.63 | 2.7–344 | 0.16 | 1.67 | 0.99 | 578 ± 60 | 17931 ± 99 |
| CPO | none | 2.7–344 | 0.04 | 0.88 | 0.94 | 80 ± 11 | 11 ± 0 |

The reaction contained either myeloperoxidase (MPO) or fungal chloroperoxidase (CPO) in 50 mM acetate buffer, pH 5.0. 1 ml final volume. Reaction was initiated by injection of 2.5 μmol $H_2O_2$.
The $V_{max}$ and v are expressed in kilocounts/10 sec (initial).
Michaelis-Menten kinetic calculations are based on the square root of the velocity, √v.

As shown in Table 5, the presence or amount of MPO or CPO in a test sample can be readily determined over a wide range of enzyme concentrations, using either bromide or chloride as the cofactor, by luminescent measurement of the indicator reaction of the invention. The luminescent response approximates second order with respect to both MPO and CPO concentrations. Under the conditions set forth in this example, MPO is more efficient than CPO; however, neither MPO or CPO functions efficiently in the absence of halide, as shown where neither chloride nor bromide was added to the indicator reaction mixture.

The foregoing procedure was followed for the bromide-dependent haloperoxidase EPO and LPO using haloperoxidase/halide solutions containing amounts of EPO ranging from 8.5 to 272 pmol and 6.3, 25 or 100 μmol of chloride; amounts of EPO ranging from 0.066 to 272 pmol and 0.63, 2.5 or 10.0 μmol of bromide; amounts of EPO ranging from 2.1 to 272 pmol and no halide; amounts of LPO ranging from 4.0 to 258 pmol and 6.3, 25 or 100 μmol of chloride; amounts of LPO ranging from 2.0 to 258 pmol and 0, 0.63, 2.5 or 10.0 μmol of bromide. The results are shown in Table 6.

TABLE 6

| | | Haloperoxidase as Primary Variable: Halide as Secondary Variable | | | | | |
|---|---|---|---|---|---|---|---|
| Reaction Conditions: | | | Rate Equation: | | | Michaelis-Menten | |
| | Halide, | [range] | $v = k[Enzyme]^i$ | | | Kinetic Data: | |
| Enzyme, | μmol | [Enzyme], pmol | (k) | (i) | ($r^2$) | $K_m \pm SE$ | $V_{max} \pm SE$ |
| EPO | Cl⁻, 100 | 8.5–272 | 0.07 | 1.96 | 0.86 | 25 ± 10 | 2127 ± 166 |
| EPO | Cl⁻, 25 | 8.5–272 | 0.01 | 2.16 | 0.86 | 117 ± 31 | 1570 ± 40 |
| EPO | Cl⁻, 6.3 | 8.5–272 | 0.00 | 2.72 | 0.97 | 400 ± 80 | 5333 ± 204 |
| EPO | Br⁻, 10 | 0.066–272 | 140.80 | 1.16 | 0.92 | 8 ± 1 | 20097 ± 17 |
| EPO | Br⁻, 2.5 | 0.066–272 | 85.50 | 1.22 | 0.95 | 14 ± 1 | 20426 ± 16 |
| EPO | Br⁻, 0.63 | 0.066–272 | 32.30 | 1.38 | 0.95 | 22 ± 2 | 18485 ± 19 |
| EPO | none | 2.1–272 | 0.02 | 1.49 | 0.94 | 547 ± 74 | 1700 ± 29 |
| LPO | Cl⁻, 100 | 4.0–258 | 0.01 | 2.43 | 0.96 | 264 ± 49 | 8745 ± 132 |
| LPO | Cl⁻, 25 | 4.0–258 | 0.00 | 2.45 | 0.97 | negative | negative |
| LPO | Cl⁻, 6.3 | 4.0–258 | 0.00 | 2.42 | 0.98 | negative | negative |
| LPO | Br⁻, 10 | 2.0–258 | 17.61 | 1.39 | 0.96 | 61 ± 2 | 29628 ± 4 |
| LPO | Br⁻, 2.5 | 2.0–258 | 1.98 | 1.76 | 0.99 | 123 ± 4 | 26203 ± 5 |
| LPO | Br⁻, 0.63 | 2.0–258 | 0.41 | 1.82 | 0.99 | 200 ± 17 | 19037 ± 47 |
| LPO | none | 2.0–258 | 0.02 | 2.08 | 0.96 | 303 ± 37 | 5435 ± 40 |

The reaction contained either eosinophil peroxidase (EPO) or lactoperoxidase (LPO) in 50 mM acetate buffer, pH 5.0, 1 ml final volume. Reaction was initiated by injection of 2.5 μmol $H_2O_2$.
The $V_{max}$ and v are expressed in kilocounts/10 sec (initial).
Michaelis-Menten kinetic calculations are based on the square root of velocity, √v.

Again, Table 6 demonstrates that both EPO and LPO can be quantitatively determined as a function of bromide dependent luminescence. Although some luminescent activity was obtained using chloride as a cofactor, both EPO and LPO exhibited magnitudinally more efficient luminescent activity in the presence of bromide. Under the reaction conditions employed, EPO exhibited more efficient luminescent activity than LPO using either bromide or chloride as a cofactor.

Example 5

Dependence on Chemiluminigenic Substrate

The dependence of the indicator reaction on the concentration of chemiluminigenic substrate was determined by following the basic procedure of Example 1 using 0.3 ml luminol solutions containing amounts of luminol ranging from 0.0018 to 15.0 nmol, as shown in Table 7, using 0.3 ml of haloperoxidase/halide solutions containing 10 pmol of MPO, EPO or HRP, and 100 µmol chloride, 10 µmol bromide or no halide, respectively, in 150 mM acetate buffer or phosphate buffer, and triggering the luminescent reaction by the addition of 0.3 ml of hydrogen peroxide solution in water containing 2.5 µmol of hydrogen peroxide. The final reaction volume was 0.9 ml. In addition, the pH of the reaction mixture was varied by using acetate buffers, pH 4.9 or 5.9, or phosphate buffers, pH 5.8 or 7.0, all at a final concentration of 50 mM, in place of the acetate buffer, pH 5.0, of Example 1. The results are shown in Table 7.

the non-haloperoxidase HRP under the more acid reaction condition. The luminescent reaction approximates first order with respect to luminol concentration in the MPO and EPO indicator reactions, but approximates second order in the HRP reaction system, confirming Dure et al., *J. Biol. Chem.*, Vol. 239, No. 7, pp. 2351 et seq., 1964, as indicated by the asterisks (*) before the Michaelis-Menten kinetics data set forth in Table 7. Consistent with the proposed haloperoxidase reaction mechanism shown in FIG. 1, these kinetic differences underscore the mechanistic differences separating the haloperoxidase from the non-haloperoxidase.

Example 6

Dependence on pH

The dependence of the indicator system on the pH of the reaction mixture was further determined by following the procedure of Example 4 using a peroxide solution containing 2.5 µmol of hydrogen peroxide to trigger the indicator reaction, using enzyme/halide solutions containing 100 µmol of chloride (as NaCl) and concentrations of enzyme ranging from 1.7 to 68 pmol as indicated in Table 8, and using 50 mM acetate buffer solutions, pH 3.7, 5.0 or 5.9, or

TABLE 7

Luminol (CLS) as Primary Variable: pH as Secondary Variable

| Reaction Conditions: | | | Rate Equation: | | | Michaelis-Menten | |
|---|---|---|---|---|---|---|---|
| Enzyme, | Buffer, | [range] | $v = k[\text{Luminol}]^i$ | | | Kinetic Data: | |
| 10 pmol | pH | [Luminol], nmol | (k) | (i) | ($r^2$) | $K_m \pm SE$ | $V_{max} \pm SE$ |
| MPO | AB 4.9 | 0.0018–15 | 95.5 | 1.02 | 0.99 | 8.80 ± 0.77 | 1490 ± 70 |
| MPO | PB 5.8 | 0.0018–15 | 1223.5 | 0.90 | 0.99 | 1.12 ± 0.06 | 2941 ± 70 |
| MPO | AB 5.9 | 0.0018–1.88 | 2632.2 | 0.83 | 0.98 | 0.41 ± 0.05 | 3211 ± 143 |
| MPO | PB 7.0 | 0.0018–0.47 | 6367.4 | 0.71 | 0.97 | 0.10 ± 0.02 | 3252 ± 219 |
| EPO | AB 4.9 | 0.0037–15 | 54.6 | 0.65 | 0.99 | 8.83 ± 0.49 | 508 ± 16 |
| EPO | PB 5.8 | 0.0037–7.5 | 1666.2 | 0.44 | 0.94 | 0.22 ± 0.01 | 2514 ± 33 |
| EPO | AB 5.9 | 0.0037–1.88 | 1492.8 | 0.60 | 0.99 | 0.41 ± 0.03 | 2063 ± 54 |
| EPO | PB 7.0 | 0.0009–0.59 | 11125.1 | 0.42 | 0.98 | 0.01 ± 0.00 | 2868 ± 250 |
| HRP | AB 4.9 | 0.0147–30 | 0.0 | 0.01 | 0.09 | * 0.00 ± 0.00 | 0 ± 0 |
| HRP | PB 5.8 | 0.0293–7.5 | 1.7 | 1.27 | 0.98 | * 5.53 ± 0.39 | 74 ± 0 |
| HRP | AB 5.9 | 0.0293–7.5 | 0.4 | 0.99 | 0.95 | * 1.92 ± 0.21 | 5 ± 0 |
| HRP | PB 7.0 | 0.0018–7.5 | 24.2 | 0.89 | 0.98 | * 0.90 ± 0.17 | 189 ± 2 |

The reaction mixture contained 100 µmol Cl$^-$, 10 µmol Br$^-$, and no halide for myeloperoxidase (MPO), eosinophil peroxidase (EPO), and horse radish peroxidase (HRP), respectively, in 50 mM acetate (AB) or phosphate (PB) buffer. Reaction was initiated by injection of 2.5 µmol H$_2$O$_2$. The final volume was 0.9 ml.
The $V_{max}$ and v are expressed as peak kilocounts/sec.
The * indicates that kinetic calculations are based on the square root of the velocity, $\sqrt{v}$.

As indicated in Table 7, luminol concentration was quantitatively determined by the MPO and EPO luminescence indicator systems over a wide variety of luminol concentrations at a pH in the range of from 4.9 to 7.0. In marked contrast, luminol could not be effectively quantified using 50 mM phosphate buffer solutions, pH 5.8, 6.9 or 8.2, to maintain the pH of the indicator reaction solutions at the indicated pH levels during reaction and luminescence measurement. The results are shown in Table 8 as measured kilocounts/10 seconds.

TABLE 8 pH as Primary Variable: Enzyme with 100 µmol Cl$^-$ as Secondary Variable
Reaction Conditions:

| | 50 mM Acetate Buffer, pH | | | 50 mM Phosphate Buffer, pH | | |
|---|---|---|---|---|---|---|
| Enzyme, pmol | 3.7 | 5.0 | 5.9 | 5.8 | 6.9 | 8.2 |
| MPO, 55.0 | 4.01 | 7417.03 | 17067.50 | 12681.30 | 22669.00 | 9829.64 |
| MPO, 27.5 | 0.70 | 2346.62 | 6662.85 | 3311.63 | 16430.00 | 5881.74 |
| MPO, 13.8 | 0.25 | 807.03 | 2154.55 | 668.22 | 4677.14 | 2984.89 |

TABLE 8-continued pH as Primary Variable: Enzyme with 100 μmol Cl⁻ as Secondary Variable
Reaction Conditions:

| Enzyme, pmol | 50 mM Acetate Buffer, pH | | | 50 mM Phosphate Buffer, pH | | |
|---|---|---|---|---|---|---|
| | 3.7 | 5.0 | 5.9 | 5.8 | 6.9 | 8.2 |
| MPO, 6.9 | 0.16 | 225.97 | 384.73 | 87.34 | 750.85 | 1393.98 |
| MPO, 3.4 | 0.15 | 47.73 | 33.89 | 7.46 | 154.41 | 710.19 |
| MPO, 1.7 | 0.14 | 5.76 | 3.86 | 1.71 | 56.42 | 406.97 |
| EPO, 68.0 | 3.51 | 274.38 | 2063.65 | 4458.64 | 14696.10 | 9868.69 |
| EPO, 34.0 | 0.81 | 166.23 | 103.20 | 1452.14 | 5351.70 | 6124.69 |
| EPO, 17.0 | 0.41 | 10.93 | 27.61 | 193.86 | 670.98 | 3443.80 |
| EPO, 8.5 | 0.28 | 3.22 | 6.53 | 31.61 | 83.37 | 1936.85 |
| EPO, 4.3 | 0.15 | 3.87 | 1.50 | 5.01 | 22.24 | 867.92 |
| EPO, 2.1 | 0.14 | 1.83 | 0.33 | 1.14 | 8.35 | 255.43 |
| HRP, 57.0 | 0.16 | 17.65 | 5047.91 | 10178.40 | 14755.80 | 447.98 |
| HRP, 28.5 | 0.15 | 0.91 | 2138.12 | 5399.35 | 21262.30 | 2817.04 |
| HRP, 14.3 | 0.15 | 0.25 | 237.90 | 1572.02 | 22511.70 | 15324.80 |
| HRP, 7.1 | 0.16 | 0.18 | 13.94 | 133.06 | 17832.90 | 23908.10 |
| HRP, 3.6 | 0.16 | 0.17 | 2.33 | 4.59 | 5730.49 | 14353.80 |
| HRP, 1.8 | 0.16 | 0.16 | 0.69 | 0.85 | 327.83 | 1124.33 |
| None | 0.14 | 0.14 | 0.16 | 0.16 | 0.47 | 12.55 |

The data is in kilocounts/10 sec; the background (dark) counts were 0.13 kilocounts/10 sec
Reaction was initiated by injection of 2.5 μmol $H_2O_2$.

The foregoing procedure was followed using enzyme/halide solutions containing 2.5 μmol of bromide (as NaBr) in place of the chloride set forth above. The results are shown in Table 9, again as measured kilocounts/10 seconds.

TABLE 9 pH as Primary Variable: Enzyme with 2.5 μmol Br⁻ as Secondary Variable
Reaction Conditions:

| Enzyme, pmol | 50 mM Acetate Buffer, pH | | | 50 mM Phosphate Buffer, pH | | |
|---|---|---|---|---|---|---|
| | 3.7 | 5.0 | 5.9 | 5.8 | 6.9 | 8.2 |
| MPO, 55.0 | 240.86 | 9444.36 | 15809.30 | 11360.80 | 24132.20 | 12419.57 |
| MPO, 27.5 | 44.09 | 4316.14 | 5241.20 | 3192.92 | 17955.30 | 6373.69 |
| MPO, 13.8 | 8.90 | 1835.67 | 1937.33 | 825.74 | 5904.30 | 3868.77 |
| MPO, 6.9 | 3.06 | 585.51 | 537.54 | 177.54 | 1346.18 | 1994.96 |
| MPO, 3.4 | 1.12 | 199.86 | 122.97 | 42.85 | 340.81 | 866.14 |
| MPO, 1.7 | 0.48 | 59.15 | 32.53 | 13.89 | 164.63 | 431.86 |
| EPO, 68.0 | 237.20 | 12981.30 | 19824.30 | 16334.80 | 2397.83 | 18323.40 |
| EPO, 34.0 | 101.81 | 8270.63 | 16155.60 | 21639.60 | 11349.40 | 13922.90 |
| EPO, 17.0 | 41.30 | 5421.10 | 11185.30 | 18508.00 | 20208.00 | 9223.43 |
| EPO, 8.5 | 16.59 | 3383.85 | 7501.80 | 11316.20 | 11000.40 | 5465.15 |
| EPO, 4.3 | 7.11 | 1570.71 | 4072.32 | 5832.13 | 4350.08 | 3202.05 |
| EPO, 2.1 | 2.51 | 532.28 | 1524.13 | 2094.98 | 1547.61 | 1976.73 |
| HRP, 57.0 | 0.14 | 16.38 | 4839.70 | 11926.80 | 14969.80 | 230.58 |
| HRP, 28.5 | 0.15 | 1.27 | 1333.18 | 6425.74 | 21470.20 | 2751.63 |
| HRP, 14.3 | 0.16 | 0.29 | 147.82 | 1205.65 | 20601.80 | 12999.40 |
| HRP, 7.1 | 0.15 | 0.17 | 12.70 | 75.30 | 17460.00 | 23704.70 |
| HRP, 3.6 | 0.15 | 0.16 | 2.46 | 5.32 | 5695.05 | 10034.92 |
| HRP, 1.8 | 0.15 | 0.17 | 0.61 | 1.07 | 267.05 | 919.74 |
| None | 0.14 | 0.14 | 0.16 | 0.15 | 0.63 | 19.12 |

The data is in kilocounts/10 sec; the background (dark) counts were 0.13 kilocounts/10 sec.
Reaction was initiated by injection of 2.5 μmol $H_2O_2$.

Both MPO with chloride or bromide and EPO with bromide effectively catalyze luminol luminescence in the acid range of pH tested, as demonstrated in Tables 8 and 9. In fact, haloperoxidase dependent luminescent activities are quantitative and relatively well maintained even at pH 8.2. The sensitivity of the HRP system increases with pH. However, an inhibitory effect is noted at the higher HRP concentrations. Unlike the haloperoxidase dependent luminescent responses, HRP luminescence is essentially unaffected by the presence of halide. A non-enzymatic, base catalyzed luminescence activity is detected at the higher pH values tested. Such activity adversely limits the signal-to-noise ratio at higher pH levels where HRP is most sensitive.

Example 7

Determination of Glucose Oxidase

The use of the indicator system in the determination of the presence or amount of an analyte in a test sample through a coupled preliminary reaction was determined by analyzing test samples for glucose concentration in the following manner. 100 μl test samples containing amounts of glucose ranging from a 0.0033 to 4.44 μmol of glucose, as indicated in Table 10, were prepared by dissolving the appropriate amount of glucose in 50 mM acetate buffer, pH 5.4. Each test solution was combined with 300 μl of luminol (125 μmol) in aqueous solution and placed in a polystyrene test tube. To each test solution was added 300 μl of a glucose oxidase solution in 100 mM acetate buffer, pH 5.4, containing amounts of glucose oxidase ("GOX", Type XS, 150,000 Units/g, G-7141 Sigma Chemicals, St. Louis, Mo., U.S.A.) ranging from 2.3 to 144 pmol (1 pmol equals 0.028 Units, where 1 Unit will oxidize 1 μmol D-glucose to D-gluconic acid and hydrogen peroxide per minute at pH 5.1 and 35° C.), as indicated in Table 10. The test samples were then immediately placed in the luminometer and allowed to incubate for a predetermined incubation time ranging from 8.5 to 44.9 minutes (Incubation Time, Table 10) at ambient temperature. At the end of the predetermined incubation time, the luminescent reaction was triggered by the addition of 300 μl of a solution containing 30 pmol of MPO and 50 μmol of chloride ion (as NaCl) in a 50 mM (final concentration in 1 ml reaction mixture) acetate buffer, pH 5.4. The results are shown in Table 10. Note that the luminescence response approximates second order with respect to glucose concentration, and as such, the square root of chemiluminescence velocity was employed for calculating to determine $V_{max}$ and $K_m$ for each reaction condition using the procedure of Example 1. In Table 10 $V_{max}$ is expressed in kilocounts/10 seconds (initial).

wide range of glucose and glucose oxidase concentrations. Since the glucose oxidase catalyzed oxidation of glucose results in the production of one molecule of hydrogen peroxide for each molecule of glucose consumed, add since the production of luminescence in the indicator system is proportional to the square of the hydrogen peroxide concentration, as previously described, the measured luminescence is proportional to the square of the concentration of glucose in the test sample using this coupled reaction system (i.e., the luminescent reaction is second order with respect to glucose concentration). This result is confirmed by the results shown in Table 10.

Since the oxidation of one molecule of glucose also results in the consumption of one molecule of oxygen, the foregoing glucose/glucose oxidase coupled reaction, or other oxidase reactions, may be used with the haloperoxidase/halide luminescence indicator system as a highly sensitive assay for oxygen in a test sample by providing known, non-rate limiting amounts of oxidase and substrate (e.g., glucose) thereby leaving oxygen as the unknown variable in the coupled reaction system.

The foregoing procedure was followed using glucose oxidase solutions containing 77 pmol of glucose oxidase, glucose sample solutions containing from 0.0016 to 3.33 μmol of glucose (as indicated in Table 11), MPO/chloride solutions containing from 1.9 to 60 pmol of MPO and from 1.6 to 50 μmol of chloride (both as indicated in Table 11) and

TABLE 10

| Glucose as Primary Variable: Glucose Oxidase (GOX) as Secondary Variable | | | | | | | |
|---|---|---|---|---|---|---|---|
| Reaction Conditions: | | | Rate Equation: | | | Michaelis-Menten | |
| GOX, | Incubation | [range] | $v = k[Glucose]^i$ | | | Kinetic Data: | |
| pmol | Time, min. | [Glucose], μmol | (k) | (i) | ($r^2$) | $K_m$ ± SE | $V_{max}$ ± SE |
| 144 | 10.0 | 0.0043–1.66 | 15846 | 1.96 | 0.95 | 0.37 ± 0.03 | 12949 ± 21 |
| 144 | 28.0 | 0.0043–1.66 | 20256 | 1.96 | 0.95 | 0.37 ± 0.03 | 16503 ± 27 |
| 144 | 37.2 | 0.0033–1.66 | 22119 | 1.97 | 0.96 | 0.40 ± 0.03 | 20543 ± 22 |
| 144 | 44.9 | 0.0033–1.66 | 26305 | 2.00 | 0.96 | 0.40 ± 0.03 | 22476 ± 33 |
| 36 | 9.1 | 0.0043–1.66 | 7846 | 2.03 | 0.97 | 0.70 ± 0.08 | 13759 ± 53 |
| 36 | 26.9 | 0.0043–1.66 | 13960 | 2.00 | 0.97 | 0.46 ± 0.04 | 14497 ± 32 |
| 36 | 34.5 | 0.0043–1.66 | 16647 | 2.00 | 0.96 | 0.43 ± 0.04 | 15971 ± 28 |
| 36 | 41.0 | 0.0043–1.66 | 19502 | 1.98 | 0.96 | 0.47 ± 0.04 | 20169 ± 30 |
| 9 | 9.6 | 0.0065–2.22 | 1153 | 1.97 | 0.98 | 2.60 ± 0.77 | 18538 ± 942 |
| 9 | 26.8 | 0.0065–2.22 | 3513 | 2.05 | 0.99 | 1.53 ± 0.17 | 21615 ± 98 |
| 9 | 34.7 | 0.0065–2.22 | 4756 | 2.02 | 0.99 | 1.16 ± 0.12 | 20307 ± 74 |
| 9 | 42.5 | 0.0065–2.22 | 6002 | 2.00 | 0.98 | 1.00 ± 0.10 | 20922 ± 61 |
| 2.3 | 8.5 | 0.0174–4.44 | 72 | 1.82 | 0.95 | 5.68 ± 3.10 | 5423 ± 885 |
| 2.3 | 25.4 | 0.0174–4.44 | 304 | 2.04 | 0.99 | 8.68 ± 1.22 | 38098 ± 445 |
| 2.3 | 33.0 | 0.0174–4.44 | 468 | 2.01 | 0.99 | 6.71 ± 0.55 | 36490 ± 132 |
| 2.3 | 40.5 | 0.0130–4.44 | 651 | 2.03 | 0.99 | 4.65 ± 0.53 | 30253 ± 175 |

The specimen was incubated with GOX in acetate buffer, pH 5.4, for the time indicated. Reaction was initiated by injection of 30 pmol MPO plus 50 μmol Cl⁻, 1 ml final volume. The temperature was 22° C.
The $V_{max}$ and v are expressed in kilocounts/10 sec (initial).
Michaelis-Menten kinetic calculations are based on the square root of the velocity, √v.

As indicated by the data in Table 10, the indicator system of the invention provides a highly sensitive means for determining glucose concentration in a test sample over a incubation times of about 22.8 to about 25.8 minutes. The results are shown in Table 11, where $V_{max}$ is expressed in kilocounts/10 seconds (initial).

TABLE 11

| Glucose as Primary Variable: Myeloperoxidase (MPO) as Secondary Variable ||||||||||
|---|---|---|---|---|---|---|---|---|---|
| Reaction Conditions: |||| Rate Equation: ||| Michaelis-Menten |||
| MPO, | $Cl^-$, | Time, | [range] | $v = k[Glucose]^i$ ||| Kinetic Data: ||
| pmol | μmol | min. | [Glucose], μmol | (k) | (i) | ($r^2$) | $K_m \pm SE$ | $V_{max} \pm SE$ |
| 60.0 | 50.0 | 25.7 | 0.0016–1.11 | 39217 | 2.04 | 0.98 | 0.42 ± 0.04 | 26730 ± 67 |
| 30.0 | 25.0 | 25.8 | 0.0016–0.83 | 40514 | 1.99 | 0.99 | 0.49 ± 0.05 | 27619 ± 86 |
| 30.0 | 50.0 | 22.9 | 0.0043–2.22 | 11861 | 1.98 | 0.94 | 0.41 ± 0.04 | 14012 ± 19 |
| 15.0 | 12.5 | 25.3 | 0.0016–0.55 | 33113 | 1.96 | 0.99 | 0.42 ± 0.03 | 15359 ± 32 |
| 15.0 | 50.0 | 24.1 | 0.0065–2.22 | 6908 | 1.98 | 0.94 | 0.43 ± 0.04 | 8811 ± 11 |
| 7.5 | 6.3 | 25.0 | 0.0043–0.55 | 17342 | 1.95 | 0.96 | 0.29 ± 0.02 | 4805 ± 7 |
| 7.5 | 50.0 | 23.7 | 0.0065–2.22 | 2513 | 2.07 | 0.94 | 0.50 ± 0.05 | 4121 ± 8 |
| 3.8 | 3.1 | 23.5 | 0.0043–0.42 | 5558 | 1.85 | 0.97 | 0.24 ± 0.01 | 1243 ± 1 |
| 3.8 | 50.0 | 24.9 | 0.0065–2.22 | 1344 | 2.00 | 0.94 | 0.53 ± 0.05 | 2706 ± 6 |
| 1.9 | 1.6 | 22.9 | 0.0065–0.28 | 365 | 1.55 | 0.99 | 0.19 ± 0.01 | 101 ± 0 |
| 1.9 | 50.0 | 22.8 | 0.0260–3.33 | 279 | 1.96 | 0.91 | 0.71 ± 0.08 | 1023 ± 3 |

The indicated quantities of MPO and $Cl^-$ were injected following specimen incubation with 77 pmol GOX in 50 mM acetate buffer, pH 5.4, containing 125 nmol Luminol, 1 ml final volume. The temperature was 22° C.
The $V_{max}$ and v are expressed in kilocounts/10 sec (initial).
Michaelis-Menten kinetic calculations are based on the square root of the velocity, $\sqrt{v}$.

The results of Table 11 demonstrate that the indicator system exhibits a high degree of stability for coupled determinations of glucose concentrations over a wide range of MPO and chloride concentrations.

Example 8

Solid Phase Immunoassay For Salmonella

Preparation of γ-Globulin Fraction of Rabbit Anti-Salmonella Antisera

The γ-globulin fraction of Bacto Salmonella O antisera (Poly A-I and Vi) and Bacto Salmonella H antisera (Poly a-z) (Difco Laboratories, Detroit, Mich.) were prepared by ammonium sulfide precipitation as described in *Methods in Immunology, A Laboratory Text for Instruction and Research*, Third Edition, J. S. Garvey, N. E. Cremer, and D. H. Sussdorf, pp. 218–219, 1977, W. A. Benjamin, Inc., Reading, Mass. The ratio of O to H antisera was 3 to 1, and the total globulin protein concentration of the resulting solution was 30 mg/ml.

Coupling of Anti-Salmonella Antibodies to Magnetic Particles

The globulin fraction of Salmonella O and H antisera was coupled to magnetic particles by the gluteraldehyde method of J. L. Guesdon and S. Avrameas (*Immunoehemistry*, Vol. 14, pp. 443–447, 1971). Two sources of magnetic particles were tested: 1) Bio-Mag 4100 amine-terminated magnetic particles of 0.5 to 1.5 micron size range, 50 mg/ml suspension (Advanced Magnetics, 61 Mooney Street, Cambridge, Mass., U.S.A.), and 2) Magnogel ACA 44 magnetic particles of 40 to 80 microns size range, 100 mg/ml suspension (IBF Biotechnics, Villeneuve la Garenne, France).

Biotinylation of Anti-Salmonella Antibody 2.0 mg of affinity purified antibody specific for salmonella common structural antigen CSA-1 (Kirkegaard and Perry Laboratories, Inc., Gaithersburg, Md., U.S.A.) was dissolved in 1.0 ml of 0.1M sodium bicarbonate buffer, pH 8.3. To the antibody solution was added 0.5 mg of biotin-amido caproate N-hydroxysuccinimide ester (BAC-NHS, Sigma Chemicals) in 100 μl of dimethyl formamide (DMF), and the mixture was allowed to stand at room temperature for 1 hour. The mixture was dialyzed overnight against 0.05M phosphate buffered saline, pH 7.2, with two buffer changes, and then stored at 4° C. for further use. The above procedure was repeated using purified rabbit anti-salmonella γ-globulin prepared as described above.

Biotinylation of Bacteriophage 10 ml of bacteriophage φ27869-$β_1$, (American Type Culture Collection, Rockville, Md., U.S.A.) containing approximately $10^{11}$–$10^{12}$ plaque forming units per ml (PFU/ml) was dialyzed against 0.1M bicarbonate-saline buffer, pH 8.3, for 16 hours at 4° C. with two buffer changes. To the dialyzed material was added 75 mg of BAC-NHS dissolved in 400 μl of DMF, and the mixture was agitated on a tilt table for 15 minutes at room temperature. The suspension was then made up to 20 ml with 0.05M phosphate buffer containing 5 mM $MgSO_4$ and 80 mM NaCl, pH 6.8, and then dialyzed against the phosphate buffer for 16 hours with three buffer changes. The dialyzed material was stored at 4° C. for further use.

Preparation of Avidinized Glucose Oxidase 10 mg of affinity purified avidin (Sigma Chemicals, No. A-9275) was dissolved in 0.5 ml of 0.1M phosphate buffer, pH 6.8, adjusted to 290 mOsm with NaCl, and mixed with 2 ml of 1.25% gluteraldehyde in 0.1M phosphate buffer, pH 6.8. The mixture was agitated overnight on a tilt table at room temperature, and then dialyzed against 0.15M NaCl for 18 hours at 4° C. with two buffer changes. To 1.0 ml of the dialyzed solution was added 25 mg of glucose oxidase dissolved in 0.15M NaCl, and 200 μl of 1.0M carbonate-bicarbonate buffer, pH 9.5. The mixture was allowed to react for 2 hours at room temperature and then overnight at 4° C.

Assay Protocol 1.0 ml of a solution containing the indicated (Table 13) number of colony forming units (CFU) of *Salmonella typhimurium*, ATCC No. 14028 (American Type Culture Collection, Rockville, Md., U.S.A.), was incubated for 30 minutes with various dilutions of anti-salmonella γ-globulin fraction coated Bio-Mag particles, prepared as described above. The incubation suspension was placed in magnetic separator to separate the particles, and the particles were washed twice with 0.1M phosphate buffer, pH 7.3, to remove unbound bacteria. The particles were then resuspended in a small (approximately 200 to 500 μl volume of wash solution, and then incubated with a 1:200 dilution of stock biotinylated anti-salmonella γ-globulin fraction for 30 minutes at 35° C. The beads were again separated from the solution and washed twice, as described above. The particles were then resuspended in a small volume of wash solution. 500 µl of a 1:25 dilution of the avidinized glucose oxidase solution described above was added to the particles and the mixture was incubated for 30 minutes at 35° C. The particles were again separated and washed three times, as previously described, and then resuspended in 600 µl of 0.1M phosphate buffer, pH 5.2, containing 3.3 µmol of D-glucose and 3.0 µl of luminol. The particles were then placed in a luminometer (Berthold model 952) and incubated in the dark for 30 minutes at room temperature. 300 µl of a solution containing a mix of MPO (approximately 10 pmol) and EPO (approximately 10 pmol) and bromide (15 µmol, as NaBr) was added to the suspension and the $v_{CL}$ was measured for a period of 20 seconds. The results are shown in Table 12.

TABLE 12

CFU of *Salmonella Typhimurium* as Primary Variable
Anti-Salmonella Coated Magnetic Particles as Secondary Variable

| Anti-Salmonella coated magnetic particles (Bio-Mag) | Number of CFU *Salmonella typhimurium*/test sample | | | |
|---|---|---|---|---|
| Dilutions of Stock | 1,000 | 100 | 10 | 0 |
| 1:1,024 | 265.3 ± 10.2 | 296.6 ± 27.8 | 524.5 ± 387.5 | 0.3 ± 0.0 |
| 1:2,048 | 51.9 ± 0.5 | 52.4 ± 0.5 | 39.6 ± 9.1 | 0.3 ± 0.0 |
| 1:4,096 | 0.7 ± 0.1 | 0.8 ± 0.2 | 0.5 ± 0.0 | 0.3 ± 0.0 |
| 1:8,192 | 0.4 ± 0.1 | 0.3 ± 0.0 | 0.3 ± 0.0 | 0.3 ± 0.0 |

Units: kilocounts/20 sec. (initial) ± sample standard deviation (δn − 1)
Background: Dark Current 0.28 kilocounts/20 sec.

The foregoing procedure was followed using a 1:2000 dilution of the stock Magnogel ACA 44 particles, prepared and coated with anti-salmonella antibody as described above or as uncoated controls, using test samples containing $10^5$ CFU of *S. typhimurium*, and using none (as a control), 1:100 or 1:1000 dilutions of either biotinylated affinity purified anti-salmonella antibody, biotinylated anti-salmonella γ-globulin fraction or biotinylated bacteriophage φ27869-β$_1$, as the biotinylated Salmonella-binding species. The results are shown in Table 13 as measured kilocounts/10 seconds (initial).

TABLE 13

Comparison of Salmonella-Phage and Anti-Salmonella Antibodies

| | Magnogel ACA 44 Magnetic Particles 1:2,000 dilution of stock | |
|---|---|---|
| Biotinylated Species | Coated w/anti-Salmonella antibody | Without antibody |
| Biotinylated affinity-purified anti-salmonella antibody | | |
| 1:100 dilution of stock | 2788 ± 367 | 294 ± 25 |
| 1:1,000 dilution | 980 ± 115 | 236 ± 79 |
| None | 3 ± 0 | 4 ± 1 |
| Biotinylated γ-globulin anti-Salmonella antibody | | |
| 1:100 dilution of stock | 1155 ± 200 | 116 ± 58 |
| 1:1000 dilution | 499 ± 146 | 145 ± 37 |
| None | 14 ± 0 | 1 ± 0 |
| Biotinylated Bacteriophage | | |

TABLE 13-continued

Comparison of Salmonella-Phage and Anti-Salmonella Antibodies

| | Magnogel ACA 44 Magnetic Particles 1:2,000 dilution of stock | |
|---|---|---|
| Biotinylated Species | Coated w/anti-Salmonella antibody | Without antibody |
| φ27869-β | | |
| 1:100 dilution of stock | 1585 ± 918 | 81 ± 35 |
| 1:1000 dilution | 405 ± 198 | 85 ± 41 |

TABLE 13-continued

Comparison of Salmonella-Phage and Anti-Salmonella Antibodies

| | Magnogel ACA 44 Magnetic Particles 1:2,000 dilution of stock | |
|---|---|---|
| Biotinylated Species | Coated w/anti-Salmonella antibody | Without antibody |
| None | 14 ± 0 | 62 ± 46 |

Units: kilocounts/10 sec (initial) ± δn − 1 (sample standard deviation)
Background: Dark Current 0.12 kilocounts/10 sec.

The experimental data of Table 12 and 13 demonstrate the sensitivity of the indicator system in combination with ligand- (anti-salmonella) specific antibody as a method for detecting bacteria. The haloperoxidase/halide luminescent indicator system may be adapted to essentially any ligand/ligand binder assay. In Table 13, Salmonella detection is via antibody- or baeteriophage-specific mechanisms. The biotinylated ligand binder is linked to glucose oxidase via avidin. Incubation with a non-rate limiting concentration of glucose results in the generation of hydrogen peroxide in proportion to the glucose oxidase concentration, and thus in proportion to the Salmonella present in the sample. The haloperoxidase/halide indicator system is held constant and non rate limiting, and the luminescence detected is proportional to the hydrogen peroxide generated via the linked ligand-enzyme relationship described.

Various modifications and applications of the indicator system of the invention will be apparent from the foregoing to those skilled in the art. Any such modifications and applications are intended to be within the scope of the appended claims except insofar as precluded by the prior art.

What is claimed is:

1. A method for determining the presence or amount of an analyte selected from one member of the group consisting of peroxide, halide, haloperoxidase enzyme, chemiluminigenic substrate for said enzyme and analytes capable of producing or consuming peroxide, halide, haloperoxidase or chemiluminigenic substrate in one or more preliminary reactions, in a sample suspected of containing an unknown amount of the analyte, said method comprising contacting the sample with an assay solution comprising a known, non-rate limiting amount of the other members of the group, maintaining the pH of the assay solution in the range of about 4 to about 7, measuring at least one characteristic of light emitted by the assay solution, and comparing the characteristic of the light measured with that of a standard solution containing a known amount of the analyte as a measure of the presence or amount of the analyte in the sample.

2. The method of claim 1 wherein the analyte is peroxide or an analyte capable of producing or consuming peroxide in one or more preliminary reactions.

3. The method of claim 2 wherein the peroxide is produced in the sample in one or more preliminary reactions in which the peroxide is a reaction product and the analyte is a reactant.

4. The method of claim 2 wherein the peroxide is consumed in the sample in one or more preliminary reactions in which the peroxide and the analyte are reactants.

5. The method of claim 2 wherein the peroxide is hydrogen peroxide.

6. The method of claim 1 wherein the haloperoxidase is selected from the group consisting of myeloperoxidase, eosinophil peroxidase, lactoperoxidase and chloroperoxidase.

7. The method of claim 6 wherein the haloperoxidase is myeloperoxidase or chloroperoxidase, and the halide is bromide or chloride.

8. The method of claim 6 wherein the haloperoxidase is eosinophil peroxidase or lactoperoxidase, and the halide is bromide.

9. The method of claim 1 wherein the analyte is a halide, or an analyte capable of producing or consuming halide in one or more preliminary reactions.

10. The method of claim 9 wherein the analyte is bromide or chloride.

11. The method of claim 10 wherein the analyte is bromide, the haloperoxidase is eosinophil peroxidase or lactoperoxidase, and the peroxide is hydrogen peroxide.

12. The method of claim 10 wherein the analyte is chloride, and which further comprises determining the MPO- or CPO-dependent characteristics of the light emitted by the assay system minus the EPO- or LPO-dependent characteristics of the light emitted by the assay system as a measure of the presence or amount of chloride in the sample.

13. The method of claim 10 wherein the analyte is bromide, and which further comprises determining the EPO- or LPO-dependent characteristics of the light emitted by the assay system divided by the MPO- or CPO-dependent characteristics of the light emitted by the assay system as a measure of the presence or amount of bromide in the sample.

14. The method of claim 1 wherein the analyte is haloperoxidase.

15. The method of claim 14 wherein the haloperoxidase is myeloperoxidase or chloroperoxidase and the halide is bromide or chloride.

16. The method of claim 14 wherein the sample is a biological fluid and the amount of myeloperoxidase in the sample is determined as a measure of the amount of polymorphonuclear leukocytes or blood monocytes in the sample.

17. The method of claim 14 wherein the haloperoxidase is eosinophil peroxidase or lactoperoxidase, and the halide is bromide.

18. The method of claim 14 wherein the sample is a biological fluid and the amount of eosinophil peroxidase in the sample is determined as a measure of the amount of eosinophils in the sample.

19. The method of claim 14 wherein the peroxide is hydrogen peroxide.

20. The method of claim 1 wherein the assay solution is a homogeneous assay solution.

21. The method of claim 1 wherein the assay solution is a heterogeneous assay solution and the reagent system further comprises an insoluble phase, a first specific binding substance immobilized on the insoluble phase and having binding specificity for the analyte, and a second specific binding substance conjugated to the haloperoxidase, to an oxidase capable of generating peroxide, or to the chemiluminigenic substrate, said second specific binding substance having binding specificity for the analyte.

22. The method of claim 21 which further comprises contacting the immobilized first specific binding substance with the sample and with the second specific binding substance, separating the soluble phase from the insoluble phase, and measuring the characteristic of the light in the soluble or the insoluble phase.

23. The method of claim 21 which further comprises adjusting the pH of the assay solution to a pH in the range of about 3 to about 8 prior to measuring the characteristic emitted light.

24. The method of claim 21 wherein the haloperoxidase enzyme is selected from the group consisting of myeloperoxidase, eosinophil peroxidase, lactoperoxidase and chloroperoxidase.

25. The method of claim 24 wherein the haloperoxidase is myeloperoxidase or chloroperoxidase and the halide is bromide or chloride.

26. The method of claim 24 wherein the haloperoxidase is eosinophil peroxidase or lactoperoxidase and the halide is bromide.

27. The method of claim 21 wherein the peroxide is $H_2O_2$.

28. The method of claim 1 wherein the chemiluminigenic substrate is a cyclic hydrazide.

29. The method of claim 28 wherein the cyclic hydrazide is a 2,3-dihydro-1,4-phthalazinedione.

30. The method of claim 28 wherein the cyclic hydrazide is selected from the group consisting of luminol and isoluminol.

31. The method of claim 1 wherein the chemiluminigenic substrate is a dioxetane precursor capable of reacting with singlet-multiplicity oxygen to produce a dioxetane or a dioxetanone.

32. The method of claim 1 wherein the halide is bromide or chloride.

33. A kit for use in a chemiluminescent or chemiluminometric assay comprising at least three members of the group consisting of:

a) a haloperoxidase;

b) a peroxide;

c) a halide;

d) a chemiluminigenic substrate; and e) a buffer solution for maintaining the pH of the assay within the range of about 4 to about 7.

34. The kit of claim 33 wherein the peroxidase enzyme is selected from the group consisting of myeloperoxidase, eosinophil peroxidase, lactoperoxidase and chloroperoxidase.

35. The kit of claim 33 wherein the peroxidase is myeloperoxidase or chloroperoxidase and the halide is bromide or iodide.

36. The kit of claim 33 wherein the peroxidase is eosinophil peroxidase or lactoperoxidase and the halide is bromide.

37. The kit of claim 33 wherein the chemiluminigenic substrate is a cyclic hydrazide.

38. The kit of claim 37 wherein the cyclic hydrazide is a 2,3-dihydro-1,4-phthalazinedione.

39. The kit of claim 37 wherein the cyclic hydrazide is luminol or isoluminol.

40. The kit of claim 33 wherein the chemiluminigenic substrate is a dioxetane precursor capable of reacting with singlet multiplicity oxygen to produce a dioxetane or a dioxetanone.

* * * * *

UNITED STATES PATENT AND TRADEMARK OFFICE
CERTIFICATE OF CORRECTION

PATENT NO. : 5,556,758  
DATED : September 17, 1996  
INVENTOR(S) : R.C. Allen

Page 1 of 6

It is certified that error appears in the above-indentified patent and that said Letters Patent is hereby corrected as shown below:

| COLUMN | LINE | |
|---|---|---|
| [56] Pg. 1, col. 2 | Refs. Cited (Other Publs., Item 2) | "Weeks et al" should read --Weeks et al.-- |
| [56] Pg. 2, col. 1 | Refs. Cited (Other Publs., Item 16) | *"Infectious Disease,"* should read *--Infectious Diseases,--* |
| [56] Pg. 2, col. 2 | Refs. Cited (Other Publs., Item 30) | "Ligan-d-Receptor" should read --Ligand-Receptor-- |
| 3 | 63 | "ehemilumineseent" should read --chemiluminescent-- |
| 4 | 23 | "HO$_2$" should read --HO$_2^-$-- |
| 5 | 4 | "arialyre" should read --analyte-- |
| 5 | 15 | "enhance to" should read --enhance or-- |
| 5 | 32 | "ehemilumineseent" should read --chemiluminescent-- |
| 5 | 41 | "ehemilumineseent" should read --chemiluminescent-- |
| 5 | 57-58 | *"J. Baeteciol.,"* should read *--J. Bacteriol.,--* |

UNITED STATES PATENT AND TRADEMARK OFFICE
CERTIFICATE OF CORRECTION

PATENT NO. : 5,556,758
DATED : September 17, 1996
INVENTOR(S) : R.C. Allen

It is certified that error appears in the above-indentified patent and that said Letters Patent is hereby corrected as shown below:

| COLUMN | LINE | |
|---|---|---|
| 5 | 59 | "MPO-haldine-hydrogen" should read --MPO-halide-hydrogen-- |
| 5 | 63 | "Polymorphonuelear Leukoeytes" should read --Polymorphonuclear Leukocytes-- |
| 6 | 45 | "haloperoxidase" should read --haloperoxidases-- |
| 8 | 57 | "halogenareal" should read --halogenated-- |
| 9 | 30 | "Haloperoxidase" should read --Haloperoxidases-- |
| 9 | 31 | "halide: hydrogen" should read --halide:hydrogen-- |
| 9 | 31 | "oxidoreductase" should read --oxidoreductases-- |
| 9 | 39 | "haloperoxidase," should read --haloperoxidases,-- |
| 9 | 42 | "haloperoxidase" should read --haloperoxidases-- |
| 11 | 57-58 | "2-tert-butyl-dimethylsilyloxy-9H-fluoren-9-ylideneadaman," should read --2-tert-butyl-dimethylsilyloxy-9H-fluoren-9-ylideneadamantane, 2-hydroxy-9H-fluoren-9-ylidencadamantane,-- |

UNITED STATES PATENT AND TRADEMARK OFFICE
CERTIFICATE OF CORRECTION

PATENT NO. : 5,556,758
DATED : September 17, 1996
INVENTOR(S) : R.C. Allen

It is certified that error appears in the above-indentified patent and that said Letters Patent is hereby corrected as shown below:

| COLUMN | LINE | |
|---|---|---|
| 13 | 21 | "velocity$_{CL}$=$I_{max}$=$K[X^-]^1$" should read --velocity$_{CL}$=$I_{max}$=k$[X^-]^1$-- |
| 13 | 38 | "Cl_-dependent" should read --Cl$^-$-dependent-- |
| 13 | 43 | "Br_-dependent" should read --Br$^-$-dependent-- |
| 14 | 5 | "ehiekenpox," should read --chickenpox,-- |
| 14 | 6 | "isehemic" should read --ischemic-- |
| 14 | 6-7 | "myoeardial" should read --myocardial-- |
| 14 | 14 | "cytotoxie" should read --cytotoxic-- |
| 14 | 22 | "angloneurotic" should read --angioneurotic-- |
| 14 | 26 | "myelocytie" should read --myelocytic-- |
| 14 | 28 | "adrenoeortieal" should read --adrenocortical-- |
| 14 | 28 | "uleerative" should read --ulcerative-- |
| 14 | 29 | "post-spleneetomy," should read --post-splenectomy,-- |
| 14 | 41-42 | "halopecoxidases" should read --haloperoxidases-- |

UNITED STATES PATENT AND TRADEMARK OFFICE
CERTIFICATE OF CORRECTION

PATENT NO. : 5,556,758
DATED : September 17, 1996
INVENTOR(S) : R.C. Allen

It is certified that error appears in the above-indentified patent and that said Letters Patent is hereby corrected as shown below:

| COLUMN | LINE | |
|---|---|---|
| 15 | 5 | "eases," should read --cases,-- |
| 16 | 43 | "Biolumineseenee" should read --Bioluminescence-- |
| 17 | 13 | "$H_{22}$" should read --$H_2O_2$-- |
| 18 | 63 | "Laric Acid" should read --Lactic Acid-- |
| 19 | 27 | "acetylphosphaste" should read --acetylphosphate-- |
| 20 | 13 | "pyruvate + $PO_4O_2$" should read --pyruvate + $PO_4+O_2$-- |
| 20 | 34 | "2-oxaglutarate" should read --2-oxalglutarate-- |
| 21 | 34 | "aidehyde" should read --aldehyde-- |
| 21 | 42 | "N-methylaminoacid oxidase;" should read --N-methylaminoacid oxidase,-- |
| 23 | 57 | "receptor antiligand)." should read --receptor (or antiligand).-- |
| 24 | 14-15 | "unreaetive" should read --unreactive-- |
| 24 | 16 | "immunologieal" should read --immunological-- |

UNITED STATES PATENT AND TRADEMARK OFFICE
CERTIFICATE OF CORRECTION

PATENT NO. : 5,556,758　　　　　　　　　　　　　　　Page 5 of 6
DATED : September 17, 1996
INVENTOR(S) : R.C. Allen It is certified that error appears in the above-indentified patent and that said Letters Patent is hereby corrected as shown below:

| COLUMN | LINE | |
|---|---|---|
| 24 | 20 | "intermediary" should read --intermediacy-- |
| 24 | 26 | "mierotiter" should read --microtiter-- |
| 27 (TABLE 2, | 8 line 4) | "(r2)" should read --($r^2$)-- |
| 29 | 6 | After "be" delete --.-- |
| 29 | 56 | "BPO" should read --EPO-- |
| 30 | 20 | "haloperoxidase" should read --haloperoxidases-- |
| 32 (TABLE 5, | 13 line 6 of last column) | "50306 ± 82" should read --50308 ± 82-- |
| 31 | 65 | "haloperoxidase" should read --haloperoxidases-- |
| 34 | 11 | "haloperoxidase from the non-haloperoxidase." should read --haloperoxidases from the non-haloperoxidases.-- |
| 38 | 4 | "add" should read --and-- |
| 39 | 50 | "*Immunoehemistry*," should read --*Immunochemistry*,-- |

UNITED STATES PATENT AND TRADEMARK OFFICE
CERTIFICATE OF CORRECTION

PATENT NO. : 5,556,758
DATED : September 17, 1996
INVENTOR(S) : R.C. Allen

It is certified that error appears in the above-indentified patent and that said Letters Patent is hereby corrected as shown below:

| COLUMN | LINE | |
|---|---|---|
| 39 | 57 | "1 a Garenne," should read --la Garenne,-- |
| 41 | 9 | "3.0 µl" should read --3.0 nmol-- |
| 44 (Claim 23, | 30 line 1) | "of claim 21" should read --of claim 1-- |
| 44 (Claim 32, | 56 line 1) | "of claim i" should read --of claim 1-- |

Signed and Sealed this

Eighth Day of April, 1997

Attest:

BRUCE LEHMAN

Attesting Officer  Commissioner of Patents and Trademarks